US011439352B2

(12) United States Patent
Yavorsky et al.

(10) Patent No.: US 11,439,352 B2
(45) Date of Patent: Sep. 13, 2022

(54) MEDICAL DEVICE WITH ADHESIVE PATCH LONGEVITY

(71) Applicant: MEDTRONIC MINIMED, INC., Northridge, CA (US)

(72) Inventors: Matthew William Yavorsky, Granada Hills, CA (US); Sarnath Chattaraj, Simi Valley, CA (US); Kiem H. Dang, Thousand Oaks, CA (US); Guangping Zhang, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 712 days.

(21) Appl. No.: 16/248,623

(22) Filed: Jan. 15, 2019

(65) Prior Publication Data
US 2019/0216397 A1    Jul. 18, 2019

Related U.S. Application Data

(60) Provisional application No. 62/618,212, filed on Jan. 17, 2018.

(51) Int. Cl.
*A61B 5/00*        (2006.01)
*A61B 5/145*       (2006.01)
(Continued)

(52) U.S. Cl.
CPC .......... *A61B 5/6833* (2013.01); *A61B 5/1486* (2013.01); *A61B 5/14532* (2013.01);
(Continued)

(58) Field of Classification Search
CPC . A61B 5/14532; A61B 5/1486; A61B 5/6833; A61B 5/68335; A61M 5/14; A61M 5/1413; A61M 5/142; A61M 5/14244; A61M 5/14248; A61M 5/158; A61M 2005/1416; A61M 2005/14264; A61M 2005/14252; A61M 2005/1586;
(Continued)

(56) References Cited

U.S. PATENT DOCUMENTS

| | | | |
|---|---|---|---|
| 4,499,896 A | * | 2/1985 | Heinecke .......... A61F 13/00063 602/57 |
| 4,562,751 A | | 1/1986 | Nason et al. |

(Continued)

FOREIGN PATENT DOCUMENTS

| | | |
|---|---|---|
| CN | 1212613 A | 3/1999 |
| CN | 102429769 A | 5/2012 |

(Continued)

*Primary Examiner* — Kevin C Sirmons
*Assistant Examiner* — Alexandra Lalonde
(74) *Attorney, Agent, or Firm* — Lorenz & Kopf, LLP

(57) ABSTRACT

A medical device includes a hub and an adhesive patch coupled to the hub. The adhesive patch is to couple the hub to an anatomy. The adhesive patch defines an edge that extends along a perimeter of the adhesive patch. The medical device includes an anisotropic shim coupled to the adhesive patch along the perimeter of the adhesive patch proximate the edge to resist an uncoupling of the adhesive patch from the anatomy. The anisotropic shim has an inner periphery spaced apart from an outer periphery and the anisotropic shim is locally rigid between the inner periphery and the outer periphery.

15 Claims, 12 Drawing Sheets

(51) Int. Cl.
*A61M 5/158* (2006.01)
*A61B 5/1486* (2006.01)
*A61M 39/00* (2006.01)
*A61M 5/14* (2006.01)
*A61M 39/02* (2006.01)

(52) U.S. Cl.
CPC .............. *A61M 5/14* (2013.01); *A61M 5/158* (2013.01); *A61M 39/00* (2013.01); *A61B 2505/07* (2013.01); *A61M 2005/1586* (2013.01); *A61M 2005/1588* (2013.01); *A61M 2039/0261* (2013.01); *A61M 2205/3569* (2013.01); *A61M 2230/201* (2013.01)

(58) Field of Classification Search
CPC .. A61M 2005/1588; A61M 2005/1401; A61M 2005/1585; A61M 2039/0261; A61M 3/027; A61M 16/0683; A61M 16/0688; A61M 25/01; A61M 25/02; A61M 2025/0206; A61M 2025/0213; A61M 2025/0246; A61M 2025/0253; A61M 2025/0266; A61M 2025/0273; A61M 2025/028; A61M 2025/0233; A61M 2025/022; A61M 2025/0226; A61M 2205/02; A61M 2205/0238; A61M 2210/04; A61M 25/0097; A61M 2039/0223; A61F 13/023; A61F 13/0236
See application file for complete search history.

(56) References Cited

U.S. PATENT DOCUMENTS

| | | |
|---|---|---|
| 4,678,408 A | 7/1987 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,892,085 B2 | 5/2005 | McIvor et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,295,786 B2 | 3/2016 | Gottlieb et al. |
| 2007/0049859 A1* | 3/2007 | Propp ................ A61F 13/0203 602/58 |
| 2007/0123819 A1 | 5/2007 | Mernoe et al. |
| 2008/0269687 A1 | 10/2008 | Chong et al. |
| 2009/0299290 A1 | 12/2009 | Moberg |
| 2009/0299301 A1 | 12/2009 | Gottlieb et al. |
| 2010/0160861 A1 | 6/2010 | Causey, III et al. |
| 2013/0237928 A1* | 9/2013 | Fisher ............... A61M 25/0625 604/263 |
| 2014/0005607 A1 | 1/2014 | Elsamahy et al. |
| 2016/0015570 A1* | 1/2016 | Heinecke ............ A61F 13/0236 602/58 |
| 2016/0310665 A1* | 10/2016 | Hwang ................ A61M 5/158 |
| 2018/0243537 A1* | 8/2018 | Karim ................ A61M 25/02 |

FOREIGN PATENT DOCUMENTS

| | | |
|---|---|---|
| CN | 204699154 U | 10/2015 |
| CN | 105188623 A | 12/2015 |
| DE | 8619002 U1 | 8/1986 |
| EP | 1951340 A1 | 8/2008 |
| EP | 2789319 A1 | 10/2014 |
| WO | 2007056504 A1 | 5/2007 |

* cited by examiner

MEDICAL DEVICE WITH ADHESIVE PATCH LONGEVITY

CROSS-REFERENCE TO RELATED APPLICATION

This application claims the benefit of U.S. Provisional Application No. 62/618,212, filed on Jan. 17, 2018. The disclosure of the above referenced application is incorporated herein by reference.

FIELD

Embodiments of the subject matter described herein relate generally to medical devices, such as those which are coupled to an anatomy with an adhesive patch. More particularly, embodiments of the subject matter relate to a medical device that has a shim that provides adhesive patch longevity.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices require an insertion set, such as an infusion set, to be coupled to the body of a user for the delivery of the insulin. Generally, the infusion set is coupled to the fluid infusion device via hollow tubing, which provides a fluid flow path from the fluid infusion device to the user. The infusion set requires a portion of a cannula, for example, to be inserted under the skin of the user to deliver the controlled amounts of insulin from the fluid infusion device to the user via the infusion set while the infusion set is coupled to the body of the user.

Typically, the infusion set is coupled to the body of the user with an adhesive patch. In certain instances, due to forces acting on the infusion set or a movement of the user, for example, an edge of the adhesive patch may peel off the skin of the user. The peeling of an edge of the adhesive may propagate throughout the adhesive patch, which may uncouple the infusion set from the body of the user. In other instances, the peeling of the edge of the adhesive patch may snag on other items, such as clothing, and result in an uncoupling of the adhesive patch from the body of the user. The peeling of the adhesive patch reduces a longevity of the adhesive patch by causing the adhesive patch to be uncoupled from the user, and thus, reduces a wear life of the infusion set, which is inconvenient to a user. Further, other medical devices, such as continuous glucose sensors or monitors, patch-based fluid infusion systems, etc., which employ an adhesive patch to couple the medical device to an anatomy may also encounter instances where the adhesive patch may peel off the skin of the user due to forces acting on the medical device, for example.

Accordingly, it is desirable to provide a medical device, such as an infusion set, with adhesive patch longevity, in which a peeling of the adhesive patch is resisted by a shim coupled to the adhesive patch when the infusion set is coupled to a user. Furthermore, other desirable features and characteristics will become apparent from the subsequent detailed description and the appended claims, taken in conjunction with the accompanying drawings and the foregoing technical field and background.

SUMMARY

The techniques of this disclosure generally relate to a medical device, such as an infusion set, with adhesive patch longevity having a shim, which resists an inadvertent peeling of the adhesive patch from a body of a user.

According to various embodiments, provided is a medical device. The medical device includes a hub and an adhesive patch coupled to the hub. The adhesive patch is to couple the hub to an anatomy. The adhesive patch defines an edge that extends along a perimeter of the adhesive patch. The medical device includes an anisotropic shim coupled to the adhesive patch along the perimeter of the adhesive patch proximate the edge to resist an uncoupling of the adhesive patch from the anatomy. The shim has an inner periphery spaced apart from an outer periphery and the shim is locally rigid between the inner periphery and the outer periphery.

Also provided according to various embodiments is an infusion unit. The infusion unit includes a hub to define a fluid flow path to receive a fluid and an adhesive patch coupled to the hub. The adhesive patch is to couple the hub to an anatomy. The adhesive patch defines an edge that extends along a perimeter of the adhesive patch. The infusion unit includes an anisotropic shim coupled to the adhesive patch along the perimeter of the adhesive patch proximate the edge to resist an uncoupling of the adhesive patch from the anatomy. The shim is coupled to the adhesive patch so as to be positioned about the hub. The shim extends along a longitudinal axis and has an inner periphery spaced apart from an outer periphery, and the shim is locally rigid between the inner periphery and the outer periphery and flexible along the longitudinal axis.

Further provided according to various embodiments is an infusion unit. The infusion unit includes a hub to define a fluid flow path to receive a fluid and an adhesive patch coupled to the hub. The adhesive patch is to couple the hub to an anatomy. The adhesive patch defines an edge that extends along a perimeter of the adhesive patch. The infusion unit includes an anisotropic shim coupled to the adhesive patch along the perimeter of the adhesive patch proximate the edge to resist an uncoupling of the adhesive patch from the anatomy. The shim is coupled to the adhesive patch so as to be positioned about the hub. The shim extends along a longitudinal axis and has an inner periphery spaced apart from an outer periphery, and the inner periphery is spaced apart from the hub by a distance. The shim is locally rigid between the inner periphery and the outer periphery and flexible along the longitudinal axis.

This summary is provided to introduce a selection of concepts in a simplified form that are further described below in the detailed description. The details of one or more aspects of the disclosure are set forth in the accompanying drawings and the description below. Other features, objects, and advantages of the techniques described in this disclosure will be apparent from the description and drawings, and from the claims. This summary is not intended to identify key features or essential features of the claimed subject matter, nor is it intended to be used as an aid in determining the scope of the claimed subject matter.

BRIEF DESCRIPTION OF DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
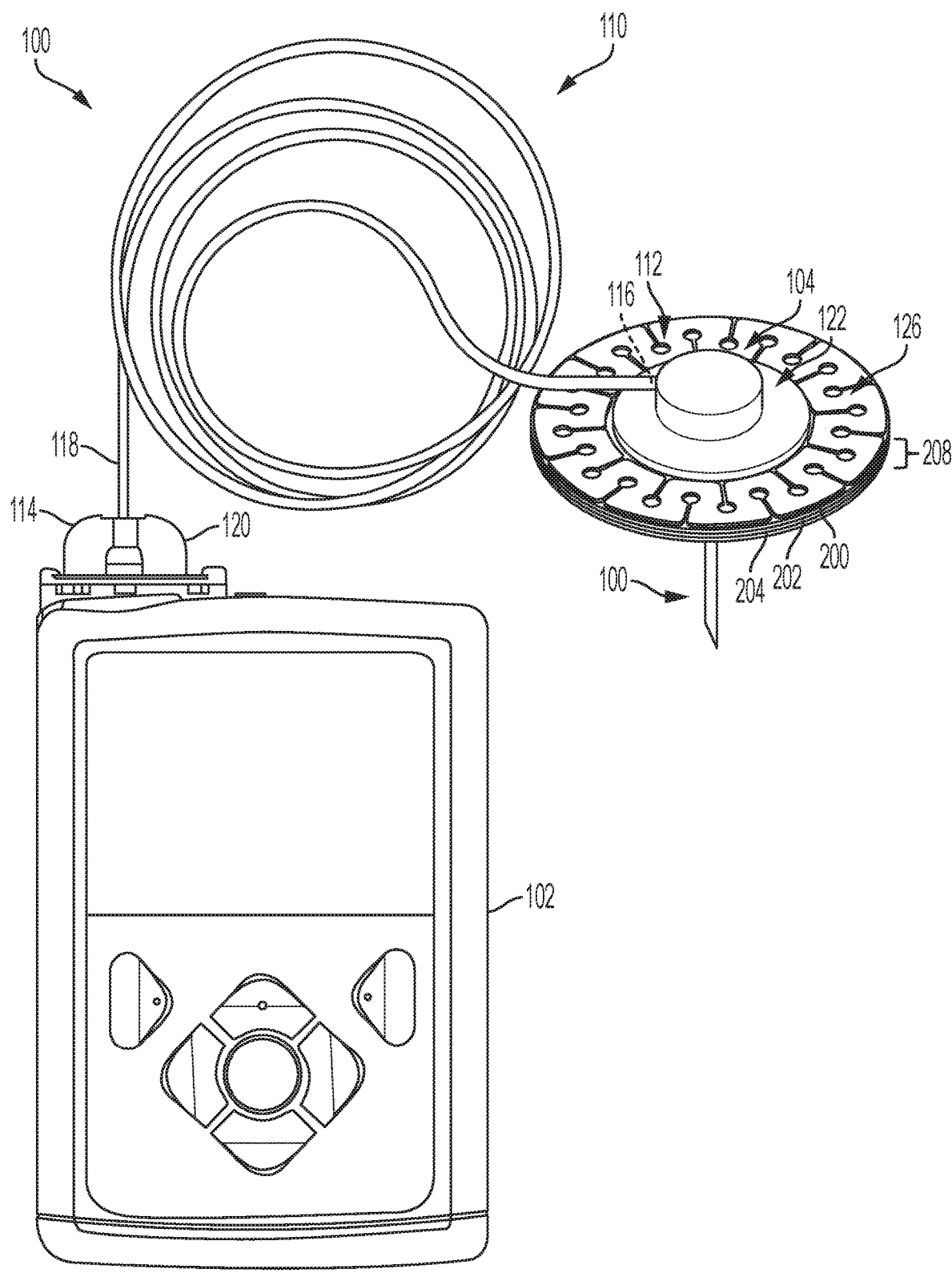
FIG. 1 is a perspective view of an exemplary fluid infusion device including a medical device, such as an infusion set, with adhesive patch longevity in accordance with various embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description generally relates to a medical device, for example, an infusion set of the type used in treating a medical condition of a user. The infusion set infuses a fluid into a body of the user. The non-limiting examples described below relate to an infusion set used in the treatment of diabetes, although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a perspective view of an exemplary embodiment of a fluid infusion system 100. The fluid infusion system 100 includes two main components: a fluid infusion device 102 (e.g., an insulin pump) and an infusion set 104, which is coupled to the fluid infusion device 102 as depicted in FIG. 1. In one example, the infusion set 104 includes, without limitation: a hollow fluid supply line or tube 110, a medical device or an infusion unit 112 and a connector assembly 114. The infusion unit 112 is coupled to a first end 116 of the tube 110 and the connector assembly 114 is coupled to a second end 118 of the tube 110. The fluid infusion device 102 is carried or worn by the user, and the infusion set 104 terminates at the infusion unit 112 to enable the fluid infusion device 102 to deliver fluid to the body of the user via the tube 110. Thus, the infusion unit 112 is coupled to the body of the user, as described in more detail below. The fluid infusion device 102 may leverage a number of conventional features, components, elements, and characteristics of existing fluid infusion devices. For example, the fluid infusion device 102 may incorporate some of the features, components, elements, and/or characteristics described in U.S. Pat. Nos. 6,485,465 and 7,621,893, the relevant content of which is incorporated by reference herein. It should be noted that the fluid infusion device 102 illustrated herein is merely exemplary, as any suitable fluid infusion device can be employed with the infusion set 104.

The fluid infusion device 102 accommodates a fluid reservoir (hidden from view in FIG. 1) for the fluid to be delivered to the user. The tube 110 represents the fluid flow path that couples the fluid reservoir to the infusion unit 112. When installed as depicted in FIG. 1, the tube 110 extends from the fluid infusion device 102 to the infusion unit 112, which in turn provides a fluid pathway to the body of the user. For the illustrated embodiment, the connector assembly 114 is realized as a removable reservoir cap 120 (or fitting) that is suitably sized and configured to accommodate replacement of fluid reservoirs (which are typically disposable) as needed. In this regard, the reservoir cap 120 is designed to accommodate the fluid path from the fluid reservoir to the tube 110.

Figure 2:
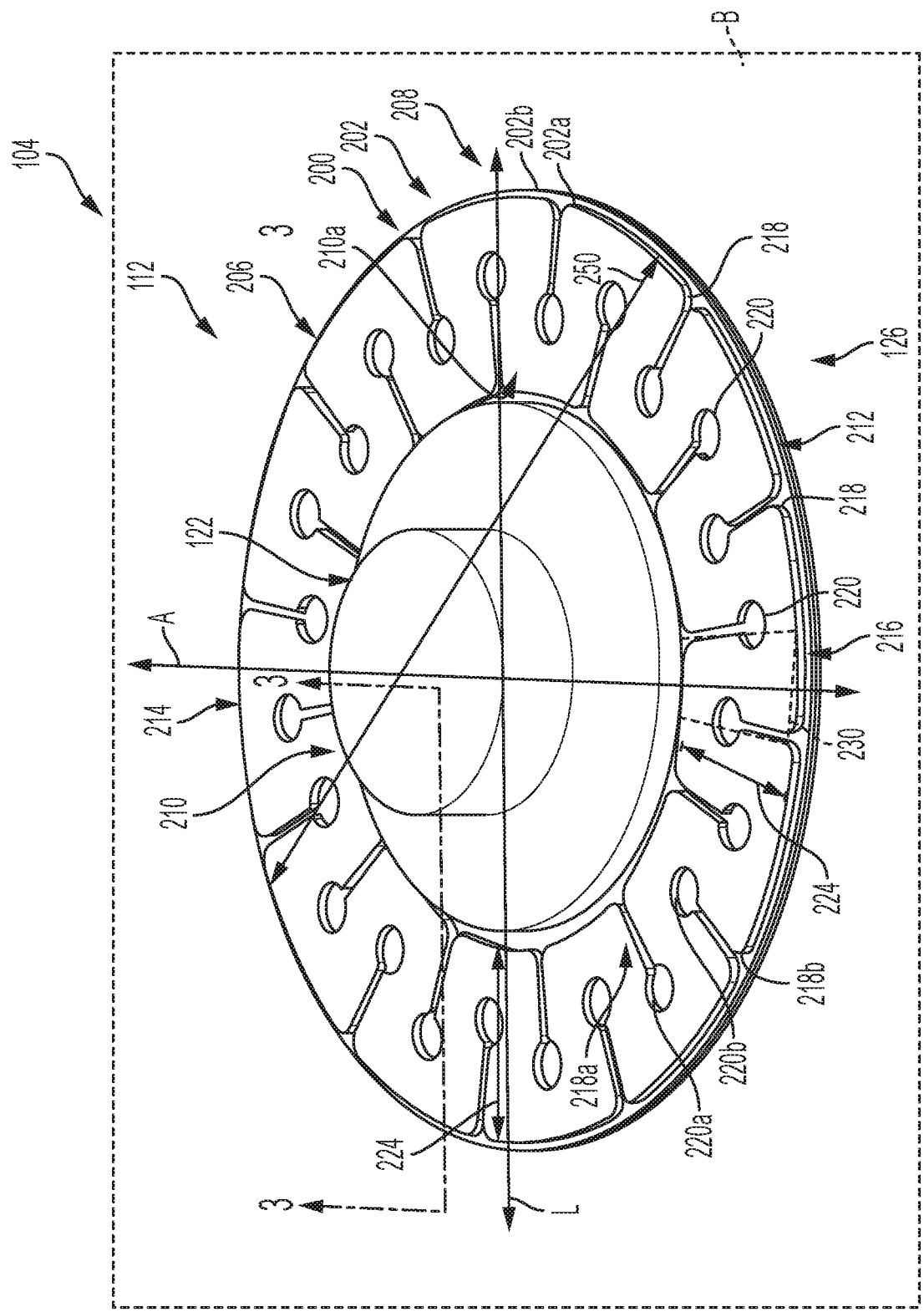
FIG. 2 is a perspective view of the infusion set of FIG. 1, which includes an extender or shim for adhesive patch longevity in accordance with various embodiments.

With reference to FIG. 2, the infusion unit 112 of the infusion set 104 is shown coupled to an anatomy or a body B of a user. In FIG. 2, the tubing 110, including the first end 116, is removed for clarity. The infusion unit 112 delivers fluid from the fluid reservoir associated with the fluid infusion device 102 (FIG. 1) received through the tube 110 into the body of the user. The infusion unit 112 includes a hub 122, a coupling device 126 and a fluid outlet 128 (FIG. 1). With reference back to FIG. 1, as the hub 122 and the fluid outlet 128 may leverage a number of conventional features, such as those of the MiniMed Quick-Set® infusion set commercially available from Medtronic MiniMed, Inc. of Northridge, Calif., the hub 122 and the fluid outlet 128 are not discussed in detail herein. Briefly, in this example, the hub 122 is annular, but the hub 122 may have any desired shape and configuration to facilitate fluid flow from the tube 110 through the infusion unit 112. The hub 122 couples the infusion unit 112 to the tube 110 and enables fluid flow from the tube 110 to exit through the fluid outlet 128. Thus, generally, the hub 122 includes one or more internal passageways that are coupled to the first end 116 of the tube 110 and enable fluid communication between the tube 110 and the fluid outlet 128. In one example, the fluid outlet 128 is cannulated, and a portion of the fluid outlet 128 is received into a portion of the body of the user to enable the fluid from the fluid infusion device 102 to flow into the body of the user. In one example, a proximal end of the fluid outlet 128 is received into the body B of the user (FIG. 2), and a distal end is fluidly coupled to the first end 116 of the tube 110. The proximal end includes a piercing tip; however, the proximal end may be atraumatic. Moreover, the fluid outlet 128 may be defined by the first end 116 of the tube 110 itself, if desired.

With reference to FIG. 2, the coupling device 126 removably couples or secures the hub 122 of the infusion unit 112 to the body B of the user. In one example, the coupling device 126 includes a backing layer 200, an adhesive layer 202, a liner 204 and an extender or shim 206. The backing layer 200, the adhesive layer 202 and the liner 204 each generally include a bore that is coaxially aligned with the fluid outlet 128 to enable the fluid outlet 128 to be inserted into the body B of the user. It should be noted that the backing layer 200 and the adhesive layer 202 are illustrated herein as having a nominal thickness, but that the backing layer 200 and the adhesive layer 202 could have any suitable thickness as necessary for the manufacture of the coupling device 126.

The backing layer 200 and the adhesive layer 202 may be separately or integrally formed. The backing layer 200 couples or fixedly attaches the adhesive layer 202 to the hub 122. In one example, the backing layer 200 is composed of a polyester, polyurethane, nylon, cotton, etc., and the adhesive layer 202 is coated on or penetrated into the backing layer 200. The backing layer 200 may be coupled or secured to the hub 122 through any suitable technique, including, but not limited to, ultrasonic welding, adhesives (including, but not limited to ultraviolet light cured adhesives, heat-glued adhesives, etc.). Generally, the backing layer 200 is coupled to substantially the entirety of the hub 122 and to the shim 206. Thus, in one example, the backing layer 200 is fixedly coupled to the hub 122 and to the shim 206. It should be noted, however, that while the backing layer 200 is illustrated herein as being defined over substantially an entire surface of the coupling device 126, the backing layer 200 may be coupled to just a portion of the surface of the adhesive layer 202. For example, the backing layer 200 may be coupled to the adhesive layer 202 so as to extend over a portion of the adhesive layer 202 that corresponds with the portion of the coupling device 126 that is coupled to the hub 122 and/or the shim 206. In other words, the backing layer 200 may be sized to correspond to the size of the hub 122 and/or the shim 206, and may have a shape that may be different than a shape of the adhesive layer 202.

The adhesive layer 202 enables the infusion unit 112 to be removably coupled to the body of the user. In one example, the adhesive layer 202 is composed of a biocompatible adhesive material, including but not limited to, an acrylic-based adhesive. The liner 204 is coupled to at least a portion of the adhesive layer 202, and is removable to facilitate coupling the coupling device 126 to the user. The liner 204 also protects the adhesive layer 202. In one example, the liner 204 is composed of a silicone or wax coated paper, polyester, high-density polyethylene, etc. The backing layer 200, the adhesive layer 202 and the liner 204 cooperate to define an adhesive patch 208 for the infusion unit 112.

With reference to FIG. 2, the shim 206 is shown in greater detail. The shim 206 is coupled to the backing layer 200, and thus, the adhesive layer 202 to stiffen a periphery or edge 202a of the adhesive layer 202 locally about a perimeter 202b of the adhesive layer 202, which resists lifting up or peeling of the adhesive layer 202 from the body of the user. In this example, the shim 206 is annular to correspond with the shape of the adhesive layer 202. The shim 206 is composed of a biocompatible material, including, but not limited to, a biocompatible metal, metal alloy or polymer-based material. In the example of a biocompatible polymer-based material, the shim 206 may be composed of polycarbonate (PC), polyethylene terephthalate (PET), polyethylene terephthalate glycol-modified (PETG), polypropylene (PP), polymethyl methacrylate (PMMA), acrylonitrile butadiene styrene (ABS), etc. Generally, semicrystalline polymers provide greater resistance to chemical exposure, such as sunscreens, while amorphous polymers may provide a more robust bond to the adhesive layer 202. As a further example of a biocompatible polymer-based material, the shim 206 may be composed of an elastomeric material, including, but not limited to a thermoplastic elastomer (TPE), silicon, neoprene, ethylene propylene diene terpolymer (EPDM), etc. Generally, in the instance of the shim 206 being composed of a polymer-based material, the shim 206 may be formed to be transparent or translucent, to enable the user to view the underlying adhesive layer 202. In the example of a biocompatible metal or metal alloy material, the shim 206 may be composed of a stainless steel. The shim 206 may be formed by stamping, machining, laser cutting, water jet cutting, molding, additive manufacturing, etc.

The shim 206 includes an inner periphery 210, an outer periphery 212 opposite the inner periphery 210, a first side 214, a second side 216 opposite the first side 214, at least one or a plurality of slits 218 and at least one or a plurality of bores 220. The inner periphery 210 is proximate the hub 122 when the shim 206 is coupled to the backing layer 200 and surrounds or defines a central bore 210a through the shim 206. The central bore 210a is sized to enable the shim 206 to be positioned about or circumscribe the hub 122. In one example, with reference to FIG. 3, when the shim 206 is coupled to the adhesive patch 208, the inner periphery 210 is spaced apart from the hub 122 by a gap or first distance 222. Generally, the first distance 222 is about 0.1 millimeters (mm) to about 1.0 mm, and in this example, is about 0.5 mm. By spacing the shim 206 apart from the hub 122 by the first distance 222, the overall flexibility of the shim 206 is improved by enabling the shim 206 to move and bend independently of the hub 122 with movements of the body B. In other embodiments, the first distance 222 may be 0.0 mm, such that the inner periphery 210 is directly adjacent or coupled to the hub 122.

Figure 3:
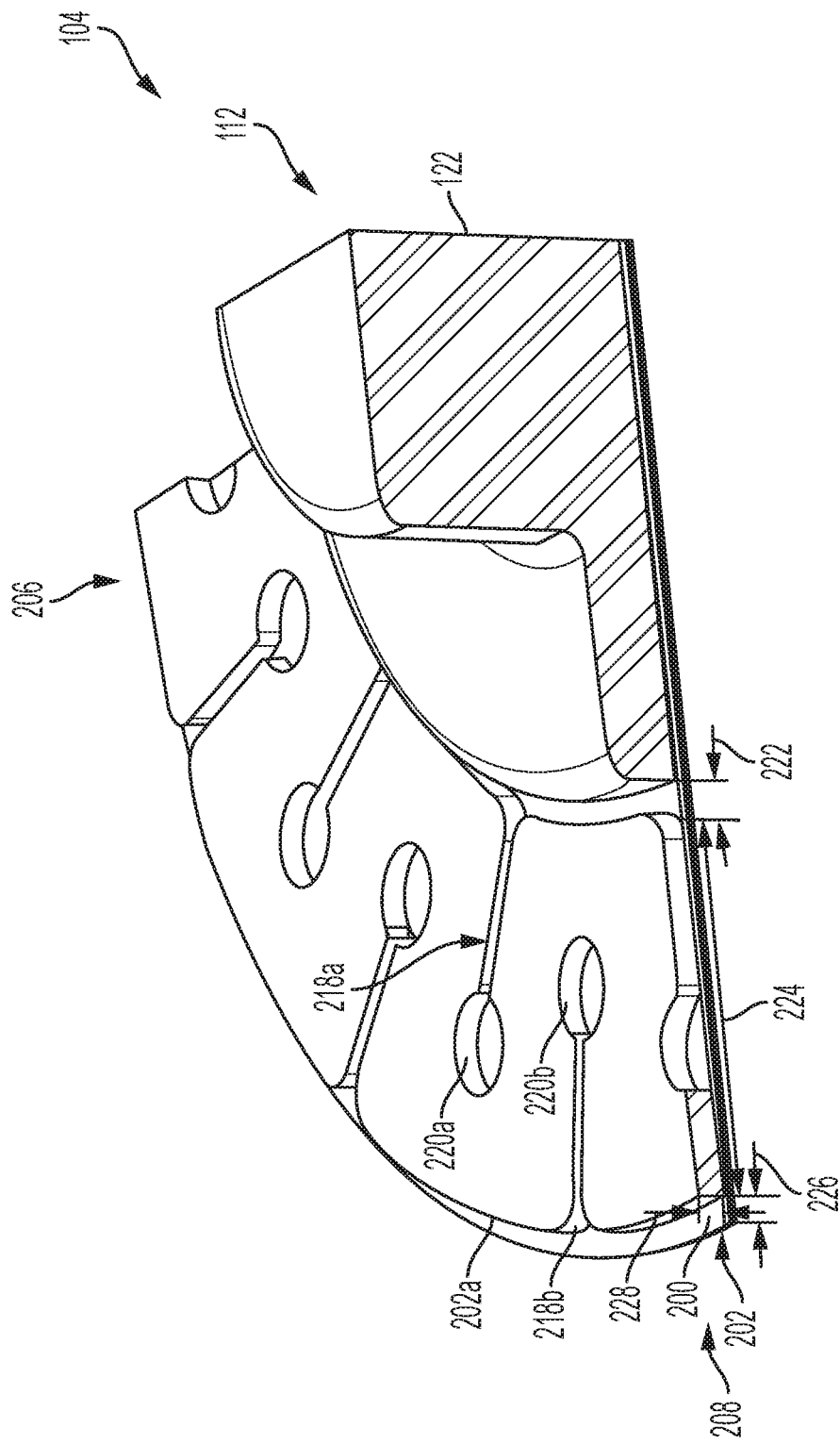
FIG. 3 is a cross-sectional view of the infusion set of FIG. 2, taken along line 3-3 of FIG. 2.
Figure 4:
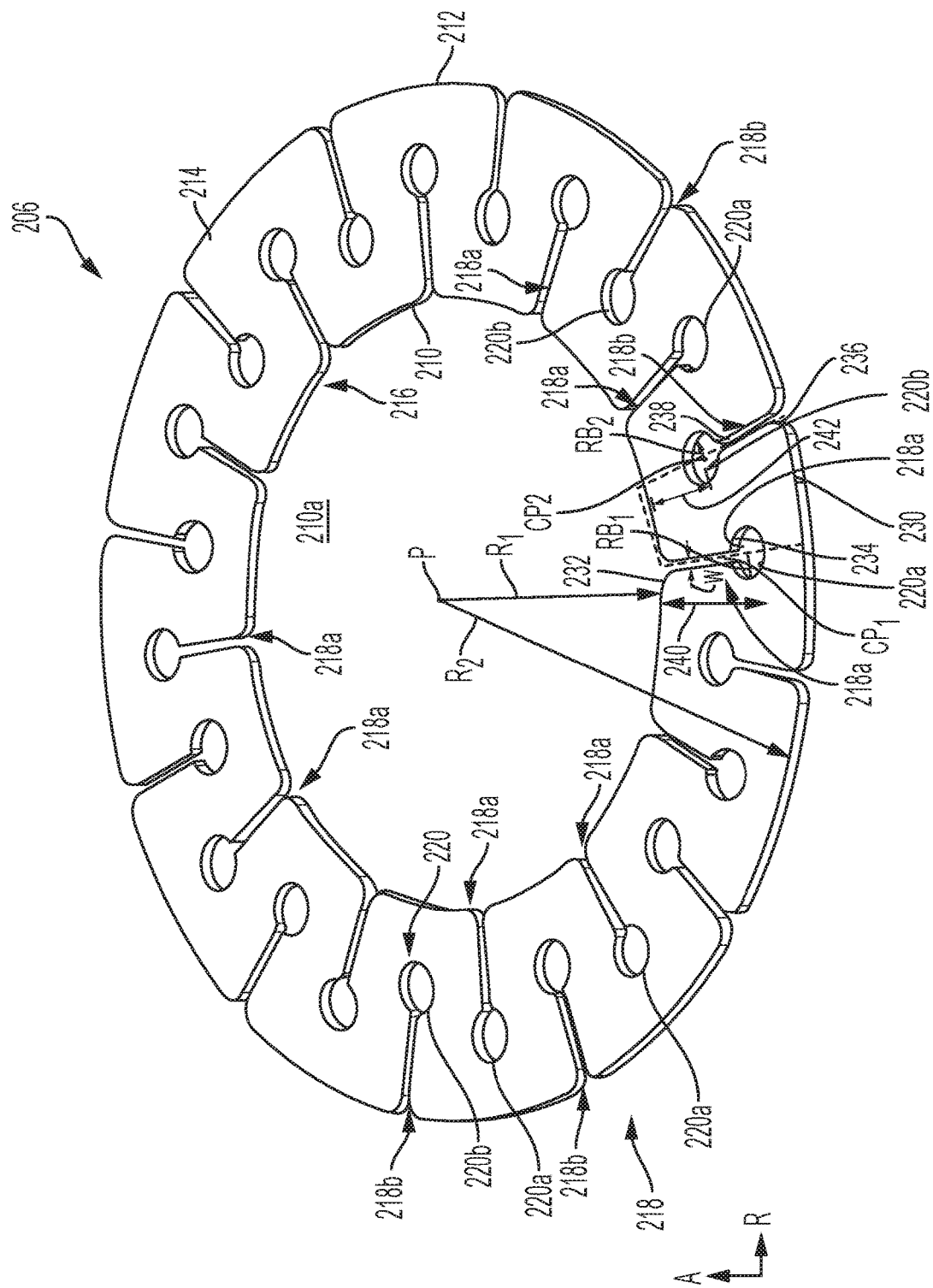
FIG. 4 is a top perspective view of the shim for use with the infusion set of FIG. 2.

With reference back to FIG. 2, the outer periphery 212 is spaced radially apart from the inner periphery 210 relative to a central axis A of the hub 122. In this example, the central axis A is also a centerline of the shim 206. The shim 206 is generally symmetric about the central axis A. With reference to FIG. 4, the shim 206 has a center point P defined on the central axis A, and the outer periphery 212 has a radius R2 from the center point P. The inner periphery 210 has a radius R1, which is less than the radius R2. With reference back to FIG. 2, a second distance 224 is defined between the outer periphery 212 and the inner periphery 210, which is different, and in this example, less than the first distance 222. With reference to FIG. 3, the outer periphery 212 is also spaced a third distance 226 apart from the perimeter 202b of the adhesive layer 202. Generally, the third distance 226 is about negative 3.0 mm to about 3.0 mm, and in this example, is about 0.5 mm. Thus, in certain embodiments, the outer periphery 212 may overhang the adhesive layer 202 to further resist against the peeling up or uncoupling of the adhesive layer 202 from the body of the user. In other embodiments, the third distance 226 may be 0.0 mm, such that the outer periphery 212 is directly aligned with the edge 202a of the adhesive layer 202.

A thickness 228 of the shim 206 is defined between the first side 214 and the second side 216. Generally, in the example of the shim 206 composed of PETG, the thickness 228 is about 0.3 mm to about 0.7 mm, and in this example, is about 0.5 mm. It should be noted, however, that the thickness 228 may vary depending on the type of material from which the shim 206 is composed. For example, a shim 206 composed of the biocompatible elastomeric material may have a greater or larger thickness than the shim 206 composed of PETG. In the instance of the shim 206 composed of the biocompatible elastomeric material, the shim 206 has the greater thickness 228, but may have increased flexibility. In the example of the shim 206 composed of a metal or metal alloy, the thickness 228 is about 0.1 mm to about 0.25 mm.

Figure 5:
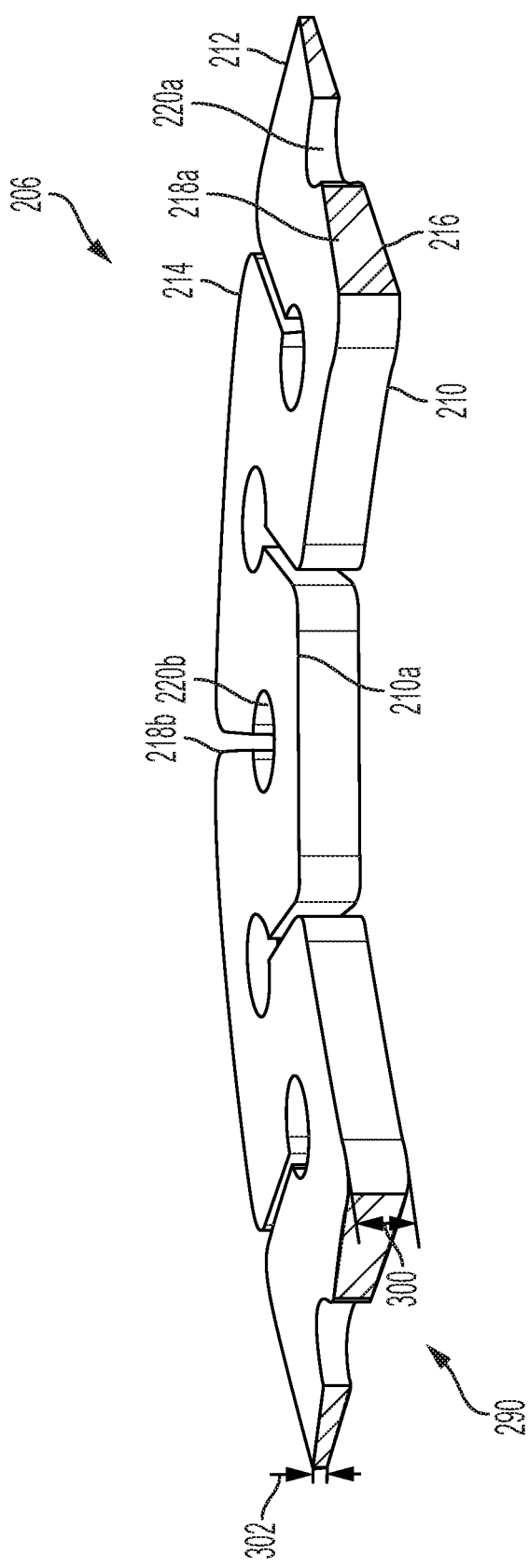
FIG. 5 is a cross-sectional view of an exemplary thickness for the shim of FIG. 4 in accordance with various embodiments.

In the example of FIGS. 1-4, the thickness 228 of the shim 206 is uniform from the inner periphery 210 to the outer periphery 212. In certain embodiments, with reference to FIG. 5, a thickness 290 of the shim 206 may vary from the inner periphery 210 to the outer periphery 212. In the example of FIG. 5, the shim 206 has a first thickness 300 at the inner periphery 210 and a second thickness 302 at the outer periphery 212, which is different, and in this example, less than the first thickness 300. The first thickness 300 is about 0.25 millimeters (mm) to about 1.0 millimeters (mm), and the second thickness 302 is about 0.05 millimeters (mm) to about 0.5 millimeters (mm). In this example, the thickness 290 of the shim 206 decreases monotonically from the first thickness 300 at the inner periphery 210 to the second thickness 302 at the outer periphery 212, but the thickness 290 may include one or more local areas of increased or decreased thickness, if desired. The decrease in thickness 290 from the first thickness 300 to the second thickness 302 results in a cross-section of the shim 206 having a wedge shape, with the shim 206 being thinner at the outer periphery 212. The thinner second thickness 302 of the outer periphery 212 reduces the snagging of the shim 206 on objects, such as clothing, etc. In addition, the thicker first thickness 300 of the inner periphery 210 may optimize part volume to reduce material waste during manufacturing of the shim 206 via molding. Generally, in the example of the shim 206 having a varied thickness, such as that shown in FIG. 5, the shim 206 may be composed of a polymer-based material, and formed by molding, machining, additive manufacturing, etc.

With reference back to FIG. 2, the first side 214 of the shim 206 forms an outermost surface of the shim 206. The first side 214 is generally planar and smooth, to reduce a likelihood of objects being snagged on the shim 206. The second side 216 is coupled to the backing layer 200. It should be noted that in other embodiments, the second side 216 may be coupled directly to the adhesive layer 202 such that the backing layer 200 may not be employed. In one example, the second side 216 is coupled to the backing layer 200 via adhesives, including pressure sensitive adhesives, time or heat cured adhesives, solvent bonding, etc. In the example of the shim 206 composed of a transparent or translucent material, light cured adhesives, such as a UV or visible light cured adhesive, may be employed to couple the shim 206 to the backing layer 200. In the example of the shim 206 composed of a rigid polymer, such as polycarbonate, polymethyl methacrylate (PMMA), acrylonitrile butadiene styrene (ABS), the shim 206 may also be coupled to the backing layer 200 via ultrasonic welding or thermal welding.

The shim 206 also includes the plurality of slits 218 and the plurality of bores 220, which are each defined through the shim 206 from the first side 214 to the second side 216. Generally, the slits 218 and the bores 220 are defined in the shim 206 in a pattern 230 that is repeated about a perimeter or circumference of the shim 206. In one example, with reference to FIG. 4, the pattern 230 of the slits 218 and the bores 220 is repeated about the circumference of the shim 206 about 12 times, however, the pattern 230 may be repeated about the perimeter or circumference of the shim 206 about 4 to about 36 times. In this example, the pattern 230 includes a first slit 218a having a first end 232 defined from the inner periphery 210 to extend radially outward toward the outer periphery 212. The first slit 218a terminates at a second end 234. The first slit 218a has a width W of about 0.1 mm to about 1.0 mm, and in one example, is about 0.2 mm to about 0.5 mm. The second end 234 of the first slit 218a is in communication with or terminates at a first bore 220a. The first bore 220a has a center point CP1. The first bore 220a generally has a radius RB1 from the center point CP1, which is less than the radius R1, and in one example, is about 0.5 millimeters (mm) to about 1.5 millimeters (mm), and in this example is about 1.0 millimeters (mm). Generally, the radius RB1 is equal to or larger than the width W of the first slit 218a to reduce the stress concentration.

The pattern 230 also includes a second slit 218b having a first end 236 defined from the outer periphery 212 to extend radially inward toward the inner periphery 210. The second slit 218b terminates at a second end 238. The second slit 218b has the width W, and the second end 238 of the second slit 218b is in communication with or terminates at a second bore 220b. The second bore 220b has a center point CP2. The second bore 220b generally has a radius RB2 from the center point CP2, which is the same as the radius RB1 of the first bore 220a. The center point CP2 of the second bore 220b is not coplanar with the center point CP1 of the first bore 220a, such that a radial distance 240 between the first bore 220a and the inner periphery 210 is different than a radial distance 242 between the second bore 220b and the inner periphery 210. Stated another way, a radial distance between the first bore 220a and the center point P is different than a radial distance between the second bore 220b and the center point P, such that the first bore 220a and the second bore 220b are radially offset relative to the center point P of the shim 206. Moreover, the first bore 220a and the second bore 220b are positioned offset from each other about the circumference of the shim 206. Thus, generally, the plurality of slits 218 includes a plurality of the first slits 218a and a plurality of the second slits 218b, which alternate about the circumference of the shim 206. The plurality of bores 220 includes a plurality of the first bores 220a and a plurality of the second bores 220b, which also alternate about the circumference of the shim 206.

In one example, with reference to FIG. 2, with the backing layer 200 coupled to the adhesive layer 202, and the liner 204 coupled to the adhesive layer 202, with the hub 122 formed and coupled to the tube 110 (FIG. 1), the hub 122 is coupled to the backing layer 200. With the shim 206 formed, the central bore 210a of the shim 206 is positioned about the hub 122 and the shim 206 is coupled to the backing layer 200 such that the inner periphery 210 is spaced apart from a periphery of the hub 122 by the first distance 222 (FIG. 3). With the shim 206 coupled to the adhesive patch 208, the infusion set 104, including the infusion unit 112, may be distributed to a user. Once received by a user, with reference to FIG. 1, the user may couple the infusion set 104 to the fluid infusion device 102 via the connector assembly 114 to establish fluid communication between the fluid infusion device 102 and the infusion unit 112. Then, the infusion unit 112 is coupled to the body B of the user. For example, the liner 204 of the coupling device 126 is removed to expose the adhesive layer 202. With reference to FIG. 2, the infusion unit 112 is coupled or inserted onto the body B of the user with an insertion device, so that at least a portion of the fluid outlet 128 extends into the body B of the user and the adhesive patch 208 is coupled to the body B of the user. With the infusion unit 112 coupled to the user, fluid from the fluid reservoir of the fluid infusion device 102 flows through the infusion unit 112 into the body B of the user and the shim 206 resists peeling of the adhesive layer 202 off the body B of the user.

In this regard, the pattern 230 of the slits 218 and the bores 220 along with the first distance 222 defined between the shim 206 and the hub 122 results in the shim 206 being very flexible over a fourth distance 250, and less flexible or rigid over the second distance 224. Stated another way, the shim 206 has a flexibility along a longitudinal axis L of the shim 206, which is different, and greater than, a flexibility of the shim 206 locally between the inner periphery 210 and the outer periphery 212 (along the second distance 224). Thus, the shim 206 is anisotropic, with increased flexibility along the longitudinal axis L of the shim 206, and is rigid locally between the inner periphery 210 and the outer periphery 212 (along the second distance 224). The overall flexibility or greater flexibility of the shim 206 over the longitudinal axis L enables the shim 206 to move with tissue of the body B underneath the adhesive layer 202, which improves user comfort. By having less flexibility or being more rigid or stiff locally between the inner periphery 210 and the outer periphery 212, the shim 206 resists the peeling up or lifting of the edge 202a of the adhesive layer 202, which prolongs a longevity of the adhesive layer 202, and thus, the adhesive patch 208. Generally, the shim 206 may extend a longevity of the adhesive patch 208 by 7 to 8 days, while maintaining overall flexibility (along the fourth distance 250). The increased longevity of the adhesive patch 208, in turn, results in an increased longevity or wear life for the infusion unit 112, which improves user satisfaction by reducing a number of replacements of the infusion unit 112. In addition, the use of the shim 206 may increase longevity of the adhesive patch 208 without requiring aggressive adhesives, which may irritate sensitive skin.

Figure 6:
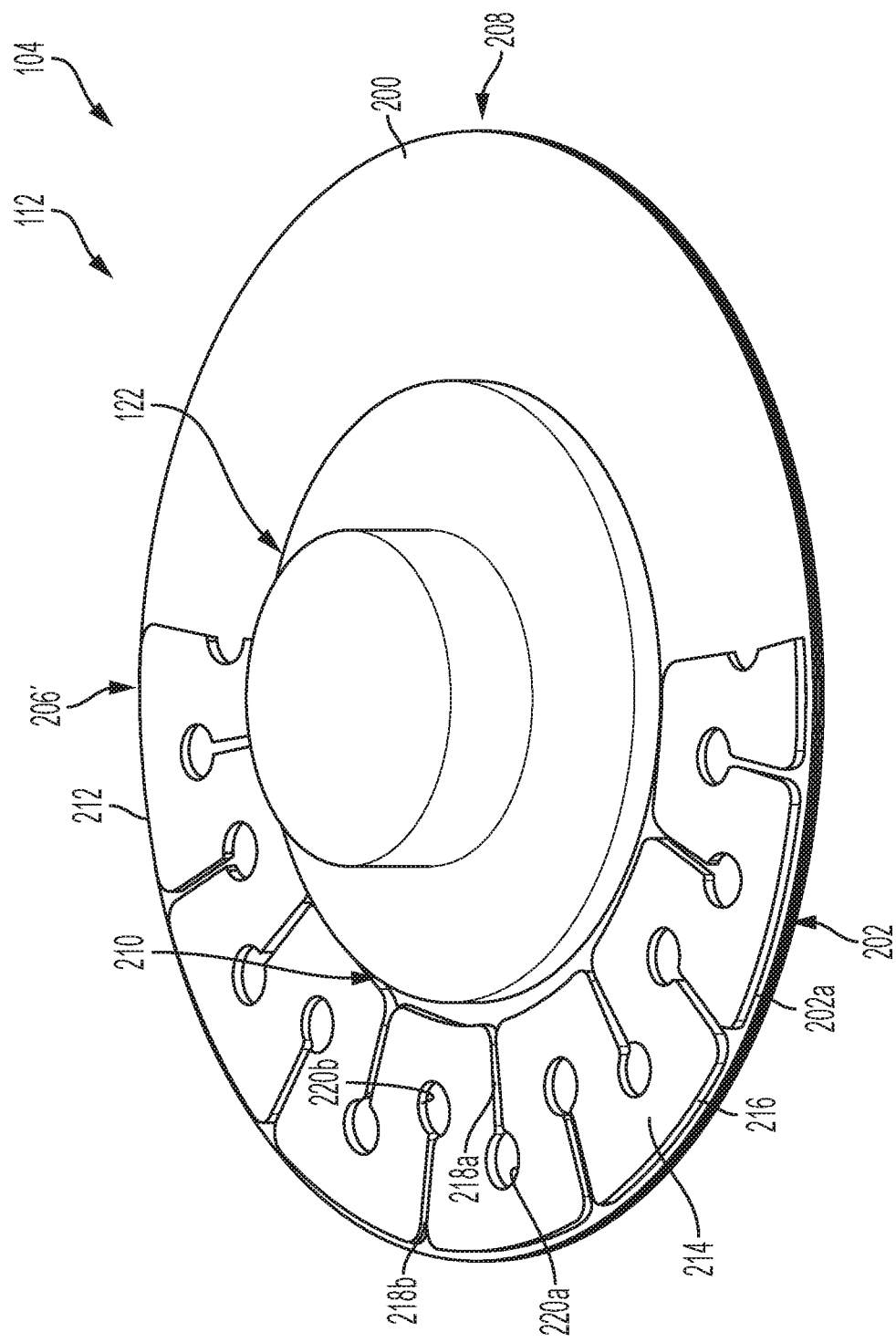
FIG. 6 is a perspective view of another exemplary infusion set with an exemplary shim for adhesive patch longevity in accordance with various embodiments.

It should be noted that in other embodiments, the shim 206 may be configured differently to extend longevity of the adhesive patch 208. For example, with reference to FIG. 6, the shim 206 need not be fully annular or need not fully surround the hub 122 to resist peeling up of the edge 202a of the adhesive layer 202. Rather, in the example of FIG. 6, a shim 206' is substantially semi-circular, and surrounds a portion of the hub 122. As the shim 206' is the same as the shim 206 discussed with regard to FIGS. 1-4, but merely has a different shape, the shim 206' will not be discussed in detail herein. By surrounding a portion of the hub 122, the shim 206' extends longevity of the adhesive patch 208 by resisting the peeling up of the edge 202a of the adhesive layer 202. It should be noted that the shim 206' may be positioned to surround any desired portion of the hub 122, and thus, the position of the shim 206' is merely an example. Moreover, the shim 206' need not be circular, but may have any shape that corresponds to the shape of the hub 122 to surround a portion of the hub 122 and extend a longevity of the adhesive patch 208.

Figure 7:
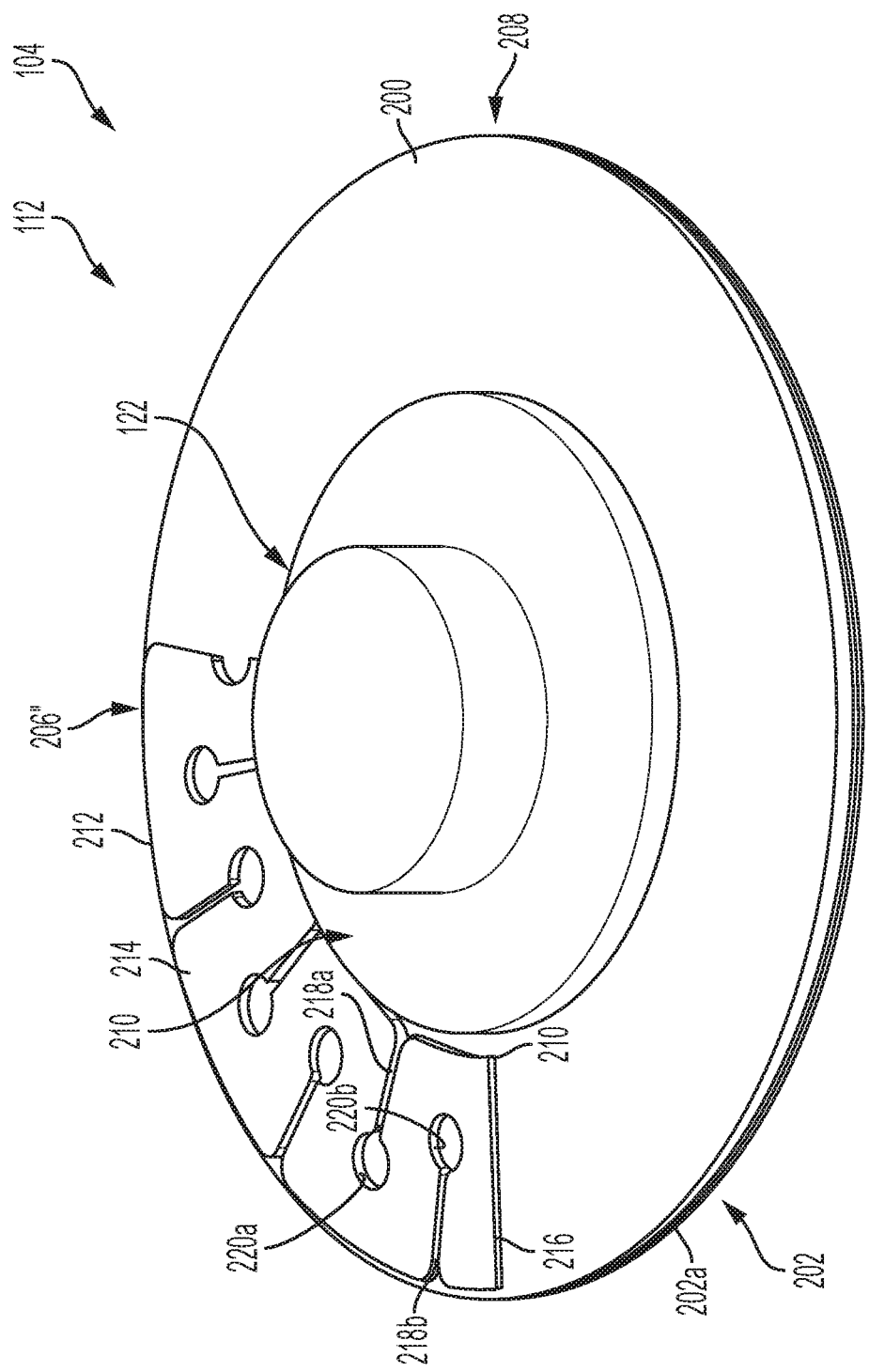
FIG. 7 is a perspective view of yet another exemplary infusion set with an exemplary shim for adhesive patch longevity in accordance with various embodiments.

It should be noted that in still other embodiments, the shim 206 may be configured differently to extend longevity of the adhesive patch 208. For example, with reference to FIG. 7, the shim 206 need not be fully annular or need not fully surround the hub 122 to resist peeling up of the edge 202a of the adhesive layer 202. Rather, in the example of FIG. 7, a shim 206" is substantially a quarter-circle, and surrounds about a quarter of the hub 122. As the shim 206" is the same as the shim 206 discussed with regard to FIGS.

1-4, but merely has a different shape, the shim 206" will not be discussed in detail herein. By surrounding a quarter of the hub 122, the shim 206" extends longevity of the adhesive patch 208 by resisting the peeling up of the edge 202*a* of the adhesive layer 202. It should be noted that the shim 206" may be positioned to surround any desired portion of the hub 122, and thus, the position of the shim 206" is merely an example. Moreover, the shim 206" need not be circular, but may have any shape that corresponds to the shape of the hub 122 to surround a quarter of the hub 122 and extend a longevity of the adhesive patch 208.

Figure 8:
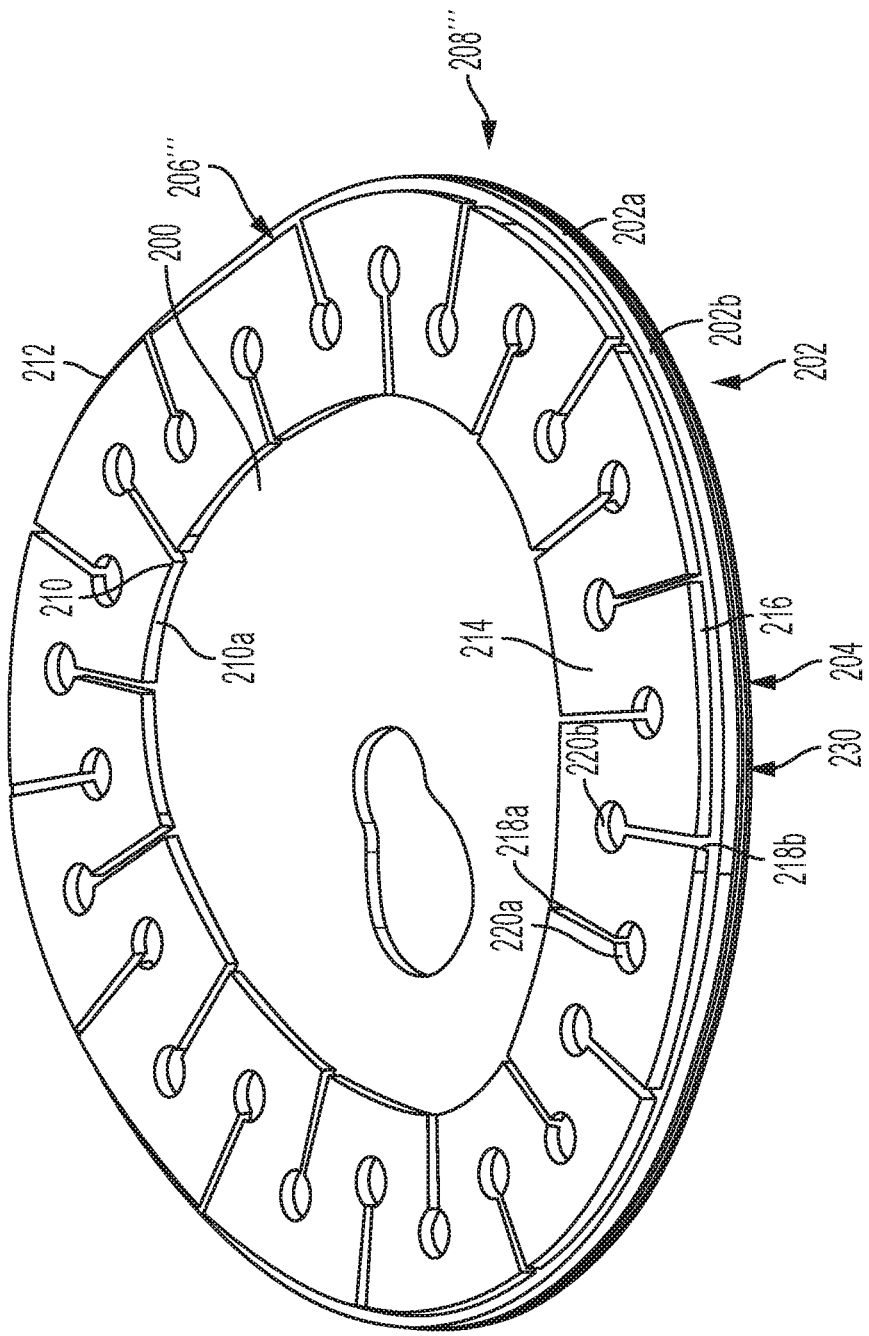
FIG. 8 is a perspective view of another exemplary shim for adhesive patch longevity for an infusion set in accordance with various embodiments.

It should be noted that in other embodiments, the shim 206 may be configured differently to extend longevity of the adhesive patch 208. For example, with reference to FIG. 8, the shim 206 need not be annular to resist peeling up of the edge 202*a* of the adhesive layer 202. Rather, in the example of FIG. 8, a shim 206''' is non-circular or trilobular to correspond with a non-circular shape of the adhesive patch 208''', which in this example, is trilobular. As the shim 206''' and the adhesive patch 208''' are each the same as the shim 206 and the adhesive patch 208 discussed with regard to FIGS. 1-4, but merely have a different shape, the shim 206''' and the adhesive patch 208''' will not be discussed in detail herein. By surrounding the perimeter 202*b* of the adhesive patch 208''', the shim 206''' extends longevity of the adhesive patch 208''' by resisting the peeling up of the edge 202*a* of the adhesive layer 202.

Figure 9:
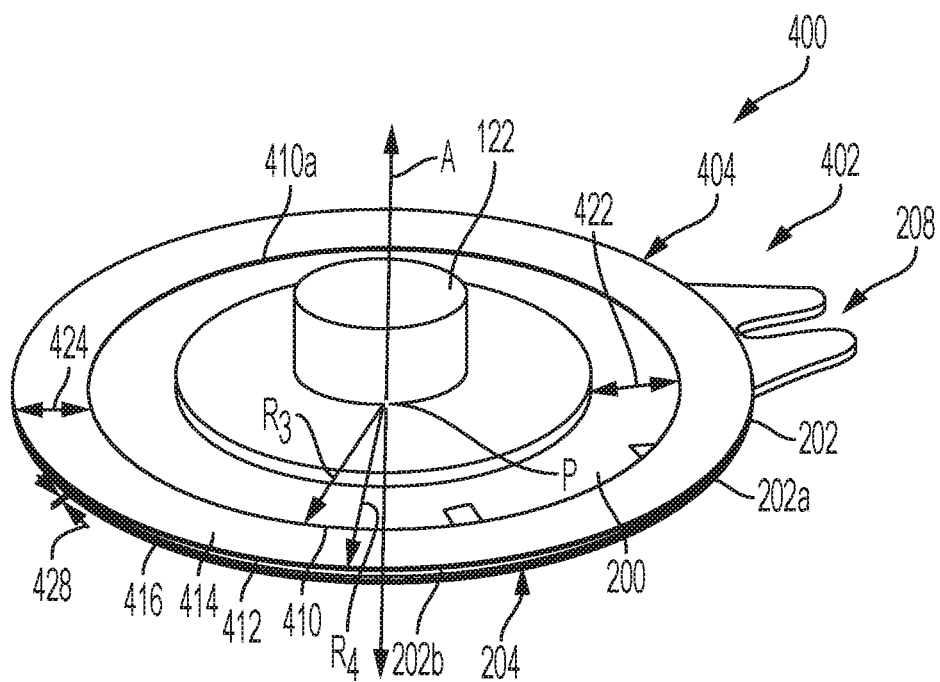
FIG. 9 is a perspective view of another exemplary infusion set with an exemplary shim for adhesive patch longevity in accordance with various embodiments.

It should be noted that in still other embodiments, the shim 206 may be configured differently to extend longevity of the adhesive patch 208. For example, with reference to FIG. 9, a medical device or an infusion unit 400 is shown. As the infusion unit 400 includes the same or similar components as the infusion unit 112 discussed with regard to FIGS. 1-4, the same reference numerals will be used to denote the same or similar components. In the example of FIG. 9, the infusion unit 400 includes the hub 122, a coupling device 402 and the fluid outlet 128 (not shown).

The coupling device 402 removably couples or secures the hub 122 of the infusion unit 400 to the body of the user. In one example, the coupling device 402 includes the backing layer 200, the adhesive layer 202, the liner 204 and an extender or shim 404. The backing layer 200, the adhesive layer 202 and the liner 204 each generally include a bore that is coaxially aligned with the fluid outlet 128 to enable the fluid outlet 128 to be inserted into the body B of the user. Generally, the backing layer 200 is coupled to substantially the entirety of the hub 122 and to the shim 404. The adhesive layer 202 enables the infusion unit 400 to be removably coupled to the body of the user. The liner 204 is coupled to at least a portion of the adhesive layer 202, and is removable to facilitate coupling the coupling device 126 to the user. The backing layer 200, the adhesive layer 202 and the liner 204 cooperate to define the adhesive patch 208 for the infusion unit 400.

The shim 404 is coupled to the backing layer 200, and thus, the adhesive layer 202 to stiffen the edge 202*a* of the adhesive layer 202 locally about a perimeter 202*b* of the adhesive layer 202, which resists lifting up or peeling of the adhesive layer 202 from the body of the user. In this example, the shim 404 is annular to correspond with the shape of the adhesive layer 202. The shim 404 is composed of a biocompatible material, including, but not limited to, a biocompatible metal, metal alloy or polymer-based material. In the example of a biocompatible polymer-based material, the shim 404 may be composed of polycarbonate (PC), polyethylene terephthalate (PET), polyethylene terephthalate glycol-modified (PETG), polypropylene (PP), polymethyl methacrylate (PMMA), acrylonitrile butadiene styrene (ABS), etc. Generally, semicrystalline polymers provide greater resistance to chemical exposure, such as sunscreens, while amorphous polymers may provide a more robust bond to the adhesive layer 202. As a further example of a biocompatible polymer-based material, the shim 404 may be composed of an elastomeric material, including, but not limited to a thermoplastic elastomer (TPE), silicon, neoprene, ethylene propylene diene terpolymer (EPDM), etc. Generally, in the instance of the shim 404 being composed of a polymer-based material, the shim 404 may be formed to be transparent or translucent, to enable the user to view the underlying adhesive layer 202. In the example of a biocompatible metal or metal alloy material, the shim 404 may be composed of a stainless steel. The shim 404 may be formed by stamping, machining, laser cutting, water jet cutting, molding, additive manufacturing, etc.

The shim 404 includes an inner periphery 410, an outer periphery 412 opposite the inner periphery 410, a first side 414 and a second side 416 opposite the first side 414. The inner periphery 410 is proximate the hub 122 when the shim 404 is coupled to the backing layer 200 and surrounds or defines a central bore 410*a* through the shim 404. The central bore 410*a* is sized to enable the shim 404 to be positioned about the hub 122. In one example, when the shim 404 is coupled to the adhesive patch 208, the inner periphery 410 is spaced apart from the hub 122 by a gap or first distance 422. Generally, the first distance 422 is about 2.0 millimeters (mm) to about 7.0 millimeters (mm), and in this example, is about 4.5 millimeters (mm). By spacing the shim 404 apart from the hub 122 by the first distance 422, the overall flexibility of the shim 404 is improved by enabling the shim 404 to move and bend independently of the hub 122 with movements of the body B. In other embodiments, the first distance 422 may be 0.0 mm, such that the inner periphery 410 is directly adjacent or coupled to the hub 122.

The outer periphery 412 is spaced radially apart from the inner periphery 410 relative to the central axis A of the hub 122. In this example, the central axis A is also a centerline of the shim 404. The shim 404 is generally symmetric about the central axis A. The shim 404 has a center point P defined on the central axis A, and the outer periphery 412 has a radius R4 from the center point P. The inner periphery 410 has a radius R3, which is less than the radius R4. A second distance 424 is defined between the outer periphery 412 and the inner periphery 410, which is different, and in this example, less than the first distance 422. The outer periphery 412 is also spaced a third distance apart from the edge 202*a* of the adhesive layer 202. In this example, the third distance is about 0.0 mm such that the outer periphery 412 is directly aligned with the edge 202*a* of the adhesive layer 202; however, in other embodiments, the third distance is about negative 3.0 mm to about 3.0 mm. Thus, in certain embodiments, the outer periphery 412 may overhang the adhesive layer 202 to further resist against the peeling up or uncoupling of the adhesive layer 202 from the body of the user.

A thickness 428 of the shim 404 is defined between the first side 414 and the second side 416. Generally, in the example of the shim 404 composed of PETG, the thickness 428 is about 0.3 mm to about 0.7 mm, and in this example, is about 0.5 mm. It should be noted, however, that the thickness 428 may vary depending on the type of material from which the shim 404 is composed. For example, a shim 404 composed of the biocompatible elastomeric material may have a greater or larger thickness than the shim 404 composed of PETG. In the instance of the shim 404 composed of the biocompatible elastomeric material, the shim 404 has the greater thickness 428, but may have increased flexibility. In the example of the shim 404 composed of a metal or metal alloy, the thickness 428 is about 0.1 mm to about 0.25 mm. In this example, the thickness 428 of the shim 404 is uniform from the inner periphery 410 to the outer periphery 412. In certain embodiments, the shim 404 may have the thickness 290 that decreases monotonically from the first thickness 300 at the inner periphery 410 to the second thickness 302 at the outer periphery 412 such that the shim 404 may have a wedge shape as discussed with regard to FIG. 5.

The first side 414 of the shim 404 forms an outermost surface of the shim 404. The first side 414 is generally planar and smooth, to reduce a likelihood of objects being snagged on the shim 404. The second side 416 is coupled to the backing layer 200. It should be noted that in other embodiments, the second side 416 may be coupled directly to the adhesive layer 202 such that the backing layer 200 may not be employed. In one example, the second side 416 is coupled to the backing layer 200 via adhesives, including pressure sensitive adhesives, time or heat cured adhesives, solvent bonding, etc. In the example of the shim 404 composed of a transparent or translucent material, light cured adhesives, such as a UV or visible light cured adhesive, may be employed to couple the shim 404 to the backing layer 200. In the example of the shim 404 composed of a rigid polymer, such as polycarbonate, polymethyl methacrylate (PMMA), acrylonitrile butadiene styrene (ABS), the shim 404 may also be coupled to the backing layer 200 via ultrasonic welding or thermal welding.

As the assembly of the shim 404 to the backing layer 200 about the hub 122 and the coupling of the infusion unit 400 to the user is substantially the same as that discussed with regard to the shim 206 of FIGS. 1-4, the assembly of the shim 404 and the coupling of the infusion unit 400 to the user will not be discussed in detail herein. Briefly, the shim 404 is coupled to the backing layer 200 so as to be spaced the first distance 422 apart from the hub 122. With the infusion unit 400 fluidly coupled to the fluid infusion device 102 (FIG. 1), the liner 204 is removed and the infusion unit 400 is coupled to the body of the user so that at least a portion of the fluid outlet 128 extends into the body B of the user and the adhesive patch 208 is coupled to the body B of the user. With the infusion unit 400 coupled to the user, fluid from the fluid reservoir of the fluid infusion device 102 flows through the infusion unit 400 into the body B of the user and the shim 404 resists peeling of the adhesive layer 202 off the body B of the user. The shim 404 is flexible overall, but is locally stiff or rigid between the inner periphery 410 and the outer periphery 412, which improves longevity of the adhesive patch 208 without reducing user comfort. Thus, the shim 404 is anisotropic, with increased flexibility along a longitudinal axis of the shim 404, and is rigid locally between the inner periphery 410 and the outer periphery 412 (along the second distance 424).

Figure 10:
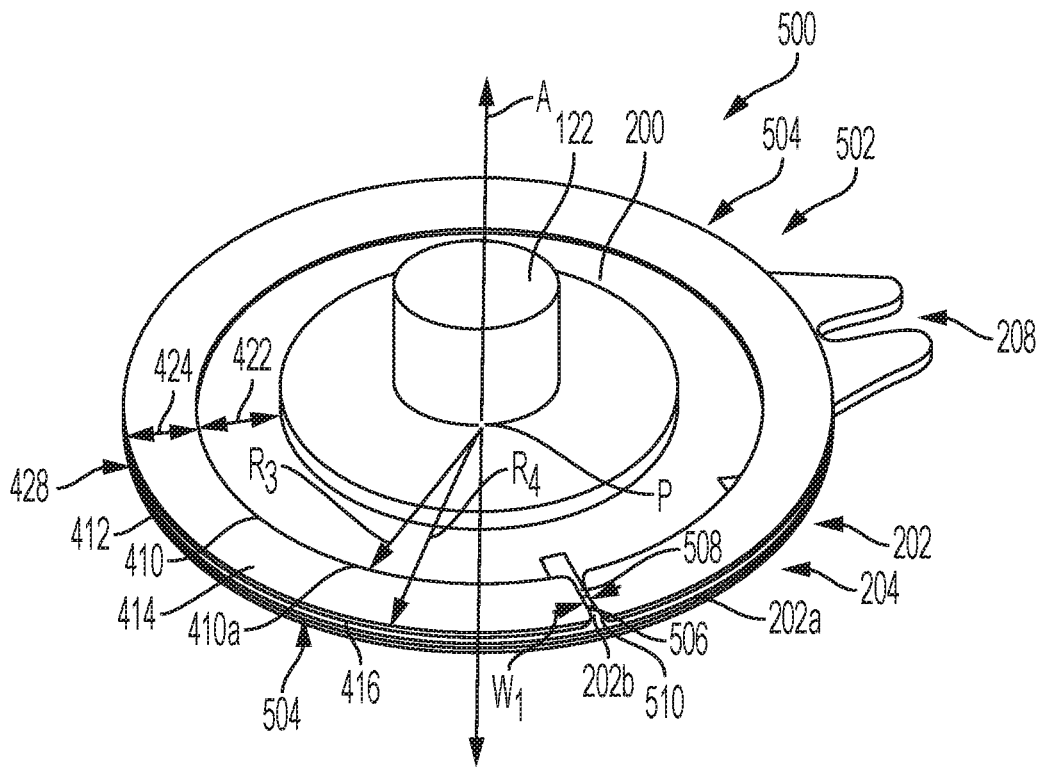
FIG. 10 is a perspective view of yet another exemplary infusion set with another exemplary shim for adhesive patch longevity in accordance with various embodiments.

It should be noted that in other embodiments, the shim 206 may be configured differently to extend longevity of the adhesive patch 208. For example, with reference to FIG. 10, a medical device or an infusion unit 500 is shown. As the infusion unit 500 includes the same or similar components as the infusion unit 112 discussed with regard to FIGS. 1-4 and the infusion unit 400 discussed with regard to FIG. 9, the same reference numerals will be used to denote the same or similar components. In the example of FIG. 10, the infusion unit 500 includes the hub 122, a coupling device 502 and the fluid outlet 128 (not shown).

The coupling device 502 removably couples or secures the hub 122 of the infusion unit 500 to the body of the user. In one example, the coupling device 502 includes the backing layer 200, the adhesive layer 202, the liner 204 and an extender or shim 504. The backing layer 200, the adhesive layer 202 and the liner 204 each generally include a bore that is coaxially aligned with the fluid outlet 128 to enable the fluid outlet 128 to be inserted into the body B of the user. Generally, the backing layer 200 is coupled to substantially the entirety of the hub 122 and to the shim 504. The adhesive layer 202 enables the infusion unit 500 to be removably coupled to the body of the user. The liner 204 is coupled to at least a portion of the adhesive layer 202, and is removable to facilitate coupling the coupling device 126 to the user. The backing layer 200, the adhesive layer 202 and the liner 204 cooperate to define the adhesive patch 208 for the infusion unit 500.

The shim 504 is coupled to the backing layer 200, and thus, the adhesive layer 202 to stiffen the edge 202a of the adhesive layer 202 locally about a perimeter 202b of the adhesive layer 202, which resists lifting up or peeling of the adhesive layer 202 from the body of the user. In this example, the shim 504 is annular to correspond with the shape of the adhesive layer 202. The shim 504 is composed of a biocompatible material, including, but not limited to, a biocompatible metal, metal alloy or polymer-based material. In the example of a biocompatible polymer-based material, the shim 504 may be composed of polycarbonate (PC), polyethylene terephthalate (PET), polyethylene terephthalate glycol-modified (PETG), polypropylene (PP), polymethyl methacrylate (PMMA), acrylonitrile butadiene styrene (ABS), etc. Generally, semicrystalline polymers provide greater resistance to chemical exposure, such as sunscreens, while amorphous polymers may provide a more robust bond to the adhesive layer 202. As a further example of a biocompatible polymer-based material, the shim 504 may be composed of an elastomeric material, including, but not limited to a thermoplastic elastomer (TPE), silicon, neoprene, ethylene propylene diene terpolymer (EPDM), etc. Generally, in the instance of the shim 504 being composed of a polymer-based material, the shim 504 may be formed to be transparent or translucent, to enable the user to view the underlying adhesive layer 202. In the example of a biocompatible metal or metal alloy material, the shim 504 may be composed of a stainless steel. The shim 504 may be formed by stamping, machining, laser cutting, water jet cutting, molding, additive manufacturing, etc.

The shim 504 includes the inner periphery 410, the outer periphery 412 opposite the inner periphery 410, the first side 414, the second side 416 opposite the first side 414 and a slit 506. The inner periphery 410 is proximate the hub 122 when the shim 404 is coupled to the backing layer 200 and surrounds or defines the central bore 410a through the shim 504. The shim 504 is spaced apart from the hub 122 by the first distance 422 to improve flexibility of the shim 504 by enabling the shim 504 to move and bend independently of the hub 122 with movements of the body B. The outer periphery 412 is spaced radially apart from the inner periphery 410 relative to the central axis A of the hub 122. The inner periphery 410 has the radius R3, which is less than the radius R4. The shim 504 also has the second distance 424 defined between the outer periphery 412 and the inner periphery 410, which is different, and in this example, less than the first distance 422. The outer periphery 412 is also spaced the third distance apart from the edge 202a of the adhesive layer 202, which in this example is 0.0 mm.

The shim 504 has the thickness 428 defined between the first side 414 and the second side 416. In this example, the thickness 428 of the shim 504 is uniform from the inner periphery 410 to the outer periphery 412. In certain embodiments, the shim 504 may have the thickness 290 that decreases monotonically from the first thickness 300 at the inner periphery 410 to the second thickness 302 at the outer periphery 412 such that the shim 504 may have a wedge shape as discussed with regard to FIG. 5.

The first side 414 of the shim 404 forms an outermost surface of the shim 504. The second side 416 is coupled to the backing layer 200. It should be noted that in other embodiments, the second side 416 may be coupled directly to the adhesive layer 202 such that the backing layer 200 may not be employed. In one example, the second side 416 is coupled to the backing layer 200 via adhesives, including pressure sensitive adhesives, time or heat cured adhesives, solvent bonding, etc. In the example of the shim 504 composed of a transparent or translucent material, light cured adhesives, such as a UV or visible light cured adhesive, may be employed to couple the shim 504 to the backing layer 200. In the example of the shim 504 composed of a rigid polymer, such as polycarbonate, polymethyl methacrylate (PMMA), acrylonitrile butadiene styrene (ABS), the shim 504 may also be coupled to the backing layer 200 via ultrasonic welding or thermal welding.

In this example, the shim 504 includes the slit 506. Generally, the slit 506 is defined through the first side 414 and the second side 416 of the shim 504. The slit 506 has a first end 508 defined at the inner periphery 410 to extend radially outward to the outer periphery 412. The slit 506 terminates at a second end 510 at the outer periphery 412. The slit 506 has a width W1 of about 0.1 mm to about 1.0 mm, and in one example, is about 0.2 mm to about 0.5 mm. The slit 506 increases a flexibility of the shim 504 as compared to the shim 404.

As the assembly of the shim 504 to the backing layer 200 about the hub 122 and the coupling of the infusion unit 500 to the user is substantially the same as that discussed with regard to the shim 206 of FIGS. 1-4, the assembly of the shim 504 and the coupling of the infusion unit 500 to the user will not be discussed in detail herein. Briefly, the shim 504 is coupled to the backing layer 200 so as to be spaced the first distance 422 apart from the hub 122. With the infusion unit 500 fluidly coupled to the fluid infusion device 102 (FIG. 1), the liner 204 is removed and the infusion unit 500 is coupled to the body of the user so that at least a portion of the fluid outlet 128 extends into the body B of the user and the adhesive patch 208 is coupled to the body B of the user. With the infusion unit 500 coupled to the user, fluid from the fluid reservoir of the fluid infusion device 102 flows through the infusion unit 500 into the body B of the user and the shim 504 resists peeling of the adhesive layer 202 off the body B of the user. The shim 504 is flexible overall, but is locally stiff or rigid between the inner periphery 410 and the outer periphery 412, which improves longevity of the adhesive patch 208 without reducing user comfort. Thus, the shim 504 is anisotropic, with increased flexibility along a longitudinal axis of the shim 504, and is rigid locally between the inner periphery 410 and the outer periphery 412 (along the second distance 424).

Figure 11:
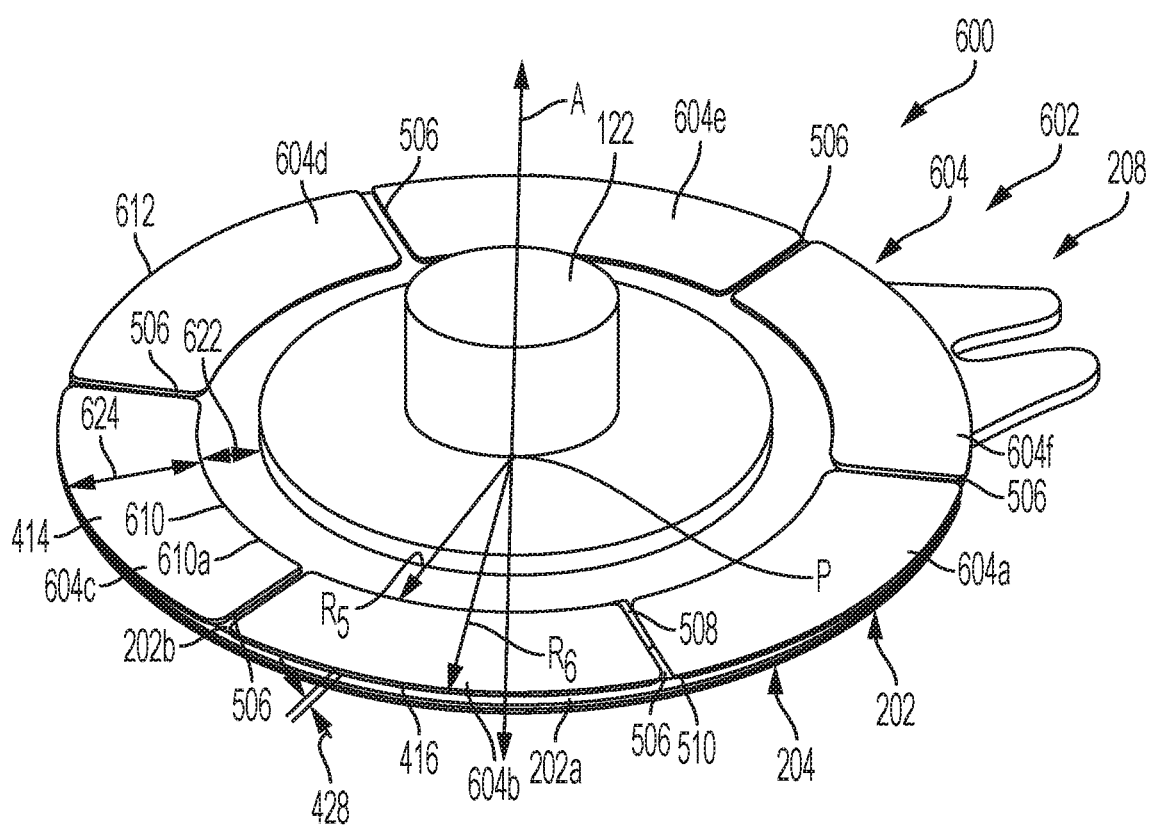
FIG. 11 is a perspective view of another exemplary infusion set with yet another exemplary shim for adhesive patch longevity in accordance with various embodiments.

It should be noted that in other embodiments, the shim 206 may be configured differently to extend longevity of the adhesive patch 208. For example, with reference to FIG. 11, a medical device or an infusion unit 600 is shown. As the infusion unit 600 includes the same or similar components as the infusion unit 112 discussed with regard to FIGS. 1-4, the infusion unit 400 discussed with regard to FIG. 9 and the infusion unit 500 discussed with regard to FIG. 10, the same reference numerals will be used to denote the same or similar components. In the example of FIG. 11, the infusion unit 600 includes the hub 122, a coupling device 602 and the fluid outlet 128 (not shown).

The coupling device 602 removably couples or secures the hub 122 of the infusion unit 600 to the body of the user. In one example, the coupling device 602 includes the backing layer 200, the adhesive layer 202, the liner 204 and an extender or shim 604. The backing layer 200, the adhesive layer 202 and the liner 204 each generally include a bore that is coaxially aligned with the fluid outlet 128 to enable the fluid outlet 128 to be inserted into the body B of the user. Generally, the backing layer 200 is coupled to substantially the entirety of the hub 122 and to the shim 604. The adhesive layer 202 enables the infusion unit 600 to be removably coupled to the body of the user. The liner 204 is coupled to at least a portion of the adhesive layer 202, and is removable to facilitate coupling the coupling device 126 to the user. The backing layer 200, the adhesive layer 202 and the liner 204 cooperate to define the adhesive patch 208 for the infusion unit 600.

The shim 604 is coupled to the backing layer 200, and thus, the adhesive layer 202 to stiffen the edge 202a of the adhesive layer 202 locally about a perimeter 202b of the adhesive layer 202, which resists lifting up or peeling of the adhesive layer 202 from the body of the user. In this example, the shim 604 is annular to correspond with the shape of the adhesive layer 202. The shim 604 is composed of a biocompatible material, including, but not limited to, a biocompatible metal, metal alloy or polymer-based material. In the example of a biocompatible polymer-based material, the shim 604 may be composed of polycarbonate (PC), polyethylene terephthalate (PET), polyethylene terephthalate glycol-modified (PETG), polypropylene (PP), polymethyl methacrylate (PMMA), acrylonitrile butadiene styrene (ABS), etc. Generally, semicrystalline polymers provide greater resistance to chemical exposure, such as sunscreens, while amorphous polymers may provide a more robust bond to the adhesive layer 202. As a further example of a biocompatible polymer-based material, the shim 604 may be composed of an elastomeric material, including, but not limited to a thermoplastic elastomer (TPE), silicon, neoprene, ethylene propylene diene terpolymer (EPDM), etc. Generally, in the instance of the shim 604 being composed of a polymer-based material, the shim 604 may be formed to be transparent or translucent, to enable the user to view the underlying adhesive layer 202. In the example of a biocompatible metal or metal alloy material, the shim 604 may be composed of a stainless steel. The shim 604 may be formed by stamping, machining, laser cutting, water jet cutting, molding, additive manufacturing, etc.

The shim 604 includes an inner periphery 610, an outer periphery 612 opposite the inner periphery 610, the first side 414, the second side 416 opposite the first side 414 and a plurality of the slits 506. In this example, the plurality of slits 506 creates a plurality of pieces or sections 604a-604f of the shim 604. In this example, the shim 604 is shown with 6 six sections 604a-604f, however, the shim 604 may have any number of sections, for example, from about 6 to about 24 sections defined by a plurality of the slits 506. Each of the sections 604a-604f is the same, and each include the inner periphery 610, the outer periphery 612, the first side 414 and the second side 416. The inner periphery 610 is proximate the hub 122 when the sections 604a-604f are each coupled to the backing layer 200 and the inner periphery 610 of the sections 604a-604f surrounds or defines a central bore 610a through the shim 604. The central bore 610a is sized to enable the shim 604 to be positioned about the hub 122. In one example, when the shim 604 is coupled to the adhesive patch 208, the inner periphery 610 is spaced apart from the hub 122 by a gap or first distance 622. Generally, the first distance 622 is about 0.1 millimeters (mm) to about 1.0 mm, and in this example, is about 0.25 mm. By spacing the shim 604 apart from the hub 122 by the first distance 622, the overall flexibility of the shim 206 is improved by enabling the shim 604 to move and bend independently of the hub 122 with movements of the body B. In other embodiments, the first distance 622 may be 0.0 mm, such that the inner periphery 610 is directly adjacent or coupled to the hub 122.

The outer periphery 612 is spaced radially apart from the inner periphery 610 relative to the central axis A of the hub 122. In this example, the central axis A is also a centerline of the shim 604. The shim 604 is generally symmetric about the central axis A. The shim 604 has a center point P defined on the central axis A, and the outer periphery 612 of each section 604a-604f has a radius R6 from the center point P. The inner periphery 610 of each section 604a-604f has a radius R5, which is less than the radius R6. A second distance 624 is defined between the outer periphery 612 of each section 604a-604f and the inner periphery 610 of each section 604a-604f, which is different, and in this example, greater than the first distance 622. The outer periphery 612 of each section 604a-604f is spaced a third distance apart from the edge 202a of the adhesive layer 202. In this example, the third distance is about 0.0 mm such that the outer periphery 612 of each section 604a-604f is directly aligned with the edge 202a of the adhesive layer 202; however, in other embodiments, the third distance is about negative 3.0 mm to about 3.0 mm. Thus, in certain embodiments, the outer periphery 612 of each section 604a-604f may overhang the adhesive layer 202 to further resist against the peeling up or uncoupling of the adhesive layer 202 from the body of the user.

Each section 604a-604f of the shim 604 has the thickness 428 defined between the first side 414 and the second side 416. In this example, the thickness 428 of the shim 604 is uniform from the inner periphery 610 to the outer periphery 612. In certain embodiments, the shim 604 may have the thickness 290 that decreases monotonically from the first thickness 300 at the inner periphery 610 to the second thickness 302 at the outer periphery 612 such that the shim 604 may have a wedge shape as discussed with regard to FIG. 5.

The first side 414 of each section 604a-604f of the shim 604 forms an outermost surface of the shim 604. The second side 416 of each section 604a-604f is coupled to the backing layer 200. It should be noted that in other embodiments, the second side 416 of each section 604a-604f may be coupled directly to the adhesive layer 202 such that the backing layer 200 may not be employed. In one example, the second side 416 of each section 604a-604f is coupled to the backing layer 200 via adhesives, including pressure sensitive adhesives, time or heat cured adhesives, solvent bonding, etc. In the example of the shim 604 composed of a transparent or translucent material, light cured adhesives, such as a UV or visible light cured adhesive, may be employed to couple the shim 604 to the backing layer 200. In the example of the shim 604 composed of a rigid polymer, such as polycarbonate, polymethyl methacrylate (PMMA), acrylonitrile butadiene styrene (ABS), the shim 604 may also be coupled to the backing layer 200 via ultrasonic welding or thermal welding.

In this example, the shim 604 includes the plurality of the slits 506 defined through the first side 414 and the second side 416 of the shim 604, which defines the sections 604a-604f. The plurality of slits 506 are spaced apart about a perimeter or circumference of the shim 604 to defined the sections 604a-604f. The plurality of the slits 506 increases a flexibility of the shim 604 as compared to the shim 206, the shim 404 and the shim 504.

As the assembly of the shim 604 to the backing layer 200 about the hub 122 and the coupling of the infusion unit 600 to the user is substantially the same as that discussed with regard to the shim 206 of FIGS. 1-4, the assembly of the shim 604 and the coupling of the infusion unit 600 to the user will not be discussed in detail herein. Briefly, each section 604a-604f of the shim 604 is coupled to the backing layer 200 so as to be spaced the first distance 622 apart from the hub 122. With the infusion unit 600 fluidly coupled to the fluid infusion device 102 (FIG. 1), the liner 204 is removed and the infusion unit 600 is coupled to the body of the user so that at least a portion of the fluid outlet 128 extends into the body B of the user and the adhesive patch 208 is coupled to the body B of the user. With the infusion unit 600 coupled to the user, fluid from the fluid reservoir of the fluid infusion device 102 flows through the infusion unit 600 into the body B of the user and the shim 604 resists peeling of the adhesive layer 202 off the body B of the user. The shim 604 is flexible overall, but is locally stiff or rigid between the inner periphery 610 and the outer periphery 612, which improves longevity of the adhesive patch 208 without reducing user comfort. Thus, the shim 604 is anisotropic, with increased flexibility along a longitudinal axis of the shim 604, and is rigid locally between the inner periphery 610 and the outer periphery 612 of each of the sections 604a-604f (along the second distance 624).

Figure 12:
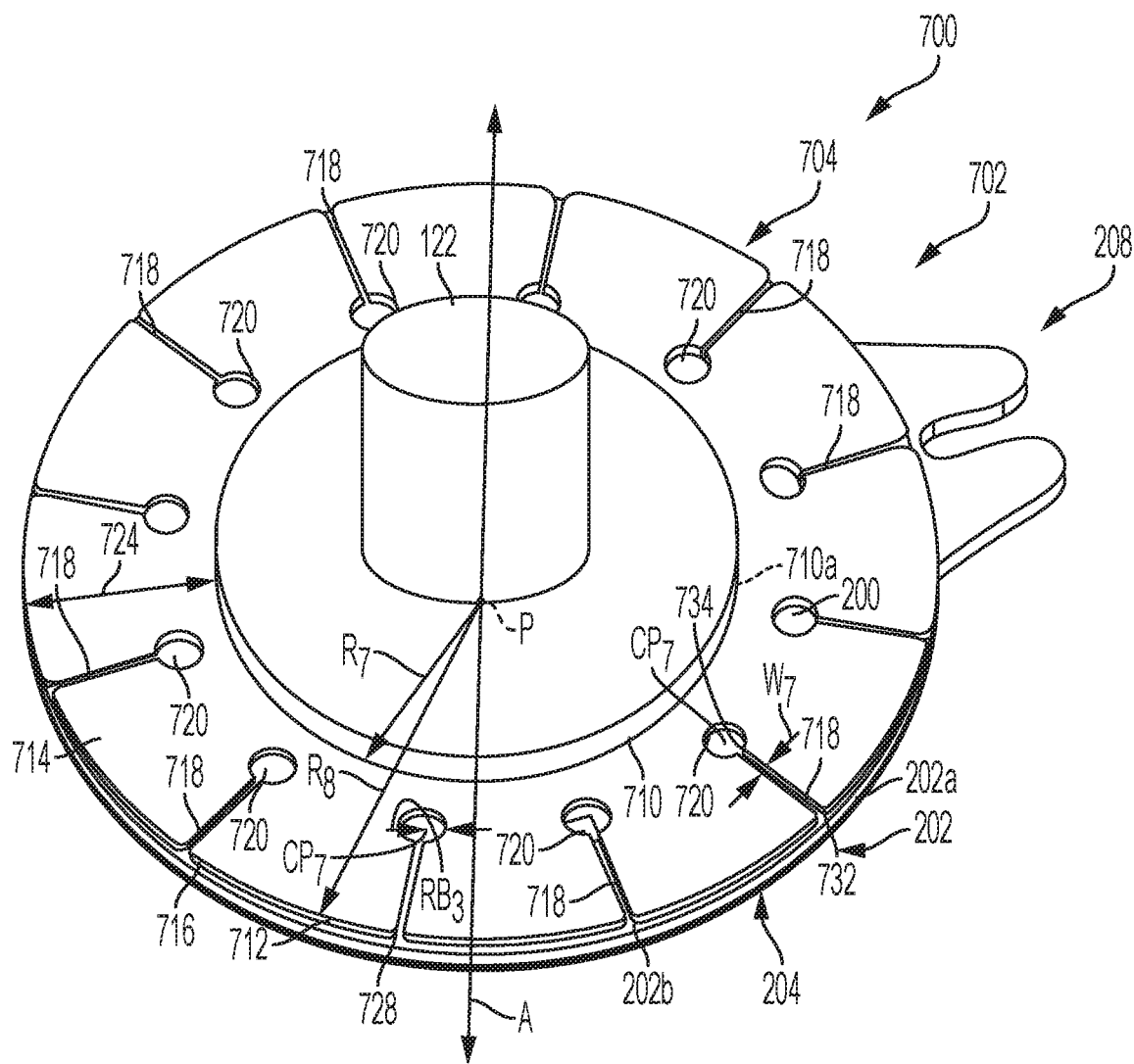
FIG. 12 is a perspective view of yet another exemplary infusion set with another exemplary shim for adhesive patch longevity in accordance with various embodiments.

It should be noted that in other embodiments, the shim 206 may be configured differently to extend longevity of the adhesive patch 208. For example, with reference to FIG. 12, a medical device or an infusion unit 700 is shown. As the infusion unit 700 includes the same or similar components as the infusion unit 112 discussed with regard to FIGS. 1-4 and the infusion unit 400 discussed with regard to FIG. 9, the same reference numerals will be used to denote the same or similar components. In the example of FIG. 12, the infusion unit 700 includes the hub 122, a coupling device 702 and the fluid outlet 128 (not shown).

The coupling device 702 removably couples or secures the hub 122 of the infusion unit 700 to the body of the user. In one example, the coupling device 702 includes the backing layer 200, the adhesive layer 202, the liner 204 and an extender or shim 704. The backing layer 200, the adhesive layer 202 and the liner 204 each generally include a bore that is coaxially aligned with the fluid outlet 128 to enable the fluid outlet 128 to be inserted into the body B of the user. Generally, the backing layer 200 is coupled to substantially the entirety of the hub 122 and to the shim 704. The adhesive layer 202 enables the infusion unit 700 to be removably coupled to the body of the user. The liner 204 is coupled to at least a portion of the adhesive layer 202, and is removable to facilitate coupling the coupling device 126 to the user. The backing layer 200, the adhesive layer 202 and the liner 204 cooperate to define the adhesive patch 208 for the infusion unit 700.

The shim 704 is coupled to the backing layer 200, and thus, the adhesive layer 202 to stiffen the edge 202a of the adhesive layer 202 locally about a perimeter 202b of the adhesive layer 202, which resists lifting up or peeling of the adhesive layer 202 from the body of the user. In this example, the shim 704 is annular to correspond with the shape of the adhesive layer 202. The shim 704 is composed of a biocompatible material, including, but not limited to, a biocompatible metal, metal alloy or polymer-based material. In the example of a biocompatible polymer-based material, the shim 704 may be composed of polycarbonate (PC), polyethylene terephthalate (PET), polyethylene terephthalate glycol-modified (PETG), polypropylene (PP), polymethyl methacrylate (PMMA), acrylonitrile butadiene styrene (ABS), etc. Generally, semicrystalline polymers provide greater resistance to chemical exposure, such as sunscreens, while amorphous polymers may provide a more robust bond to the adhesive layer 202. As a further example of a biocompatible polymer-based material, the shim 704 may be composed of an elastomeric material, including, but not limited to a thermoplastic elastomer (TPE), silicon, neoprene, ethylene propylene diene terpolymer (EPDM), etc. Generally, in the instance of the shim 704 being composed of a polymer-based material, the shim 704 may be formed to be transparent or translucent, to enable the user to view the underlying adhesive layer 202. In the example of a biocompatible metal or metal alloy material, the shim 704 may be composed of a stainless steel. The shim 704 may be formed by stamping, machining, laser cutting, water jet cutting, molding, additive manufacturing, etc.

The shim 704 includes an inner periphery 710, an outer periphery 712 opposite the inner periphery 710, a first side 714, a second side 716 opposite the first side 714, at least one or a plurality of slits 718 and at least one or a plurality of bores 720. The inner periphery 710 is proximate the hub 122 when the shim 704 is coupled to the backing layer 200 and surrounds or defines a central bore 710a through the shim 706. The central bore 710a is sized to enable the shim 704 to be positioned about the hub 122. In one example, when the shim 704 is coupled to the hub 122, the inner periphery 710 is directly adjacent to the hub 122. In other embodiments, the shim 704 may be integrally formed with the hub 122. In still other embodiments, the inner periphery 710 may be spaced apart from the hub 122 by a gap or a first distance, such as the first distance 222 discussed with regard to FIGS. 1-4.

The outer periphery 712 is spaced radially apart from the inner periphery 710 relative to the central axis A of the hub 122. In this example, the central axis A is also a centerline of the shim 704. The shim 704 is generally symmetric about the central axis A. The shim 704 has a center point P defined on the central axis A, and the outer periphery 712 has a radius R8 from the center point P. The inner periphery 710 has a radius R7, which is less than the radius R8. A second distance 724 is defined between the outer periphery 712 and the inner periphery 710. In this example, the outer periphery 712 is directly aligned with the edge 202a of the adhesive layer 202, but in other embodiments, the outer periphery 712 may be spaced apart from the edge 202a by a third distance, such as the third distance 226 discussed with regard to FIGS. 1-4.

A thickness 728 of the shim 704 is defined between the first side 714 and the second side 716. Generally, in the example of the shim 704 composed of PETG, the thickness 728 is about 0.3 mm to about 0.7 mm, and in this example, is about 0.5 mm. It should be noted, however, that the thickness 728 may vary depending on the type of material from which the shim 704 is composed. For example, a shim 704 composed of the biocompatible elastomeric material may have a greater or larger thickness than the shim 704 composed of PETG. In the instance of the shim 704 composed of the biocompatible elastomeric material, the shim 704 has the greater thickness 728, but may have increased flexibility. In the example of the shim 704 composed of a metal or metal alloy, the thickness 728 is about 0.1 mm to about 0.25 mm.

The shim 704 has the thickness 728 defined between the first side 714 and the second side 716. In this example, the thickness 728 of the shim 704 is uniform from the inner periphery 710 to the outer periphery 712. In certain embodiments, the shim 704 may have the thickness 290 that decreases monotonically from the first thickness 300 at the inner periphery 710 to the second thickness 302 at the outer periphery 712 such that the shim 704 may have a wedge shape as discussed with regard to FIG. 5.

The first side 714 of the shim 704 forms an outermost surface of the shim 704. The first side 714 is generally planar and smooth, to reduce a likelihood of objects being snagged on the shim 704. The second side 716 is coupled to the backing layer 200. It should be noted that in other embodiments, the second side 716 may be coupled directly to the adhesive layer 202 such that the backing layer 200 may not be employed. In one example, the second side 716 is coupled to the backing layer 200 via adhesives, including pressure sensitive adhesives, time or heat cured adhesives, solvent bonding, etc. In the example of the shim 704 composed of a transparent or translucent material, light cured adhesives, such as a UV or visible light cured adhesive, may be employed to couple the shim 704 to the backing layer 200. In the example of the shim 704 composed of a rigid polymer, such as polycarbonate, polymethyl methacrylate (PMMA), acrylonitrile butadiene styrene (ABS), the shim 704 may also be coupled to the backing layer 200 via ultrasonic welding or thermal welding.

The shim 704 also includes the plurality of slits 718 and the plurality of bores 720, which are each defined through the shim 704 from the first side 714 to the second side 716. Generally, the slits 718 and the bores 720 are defined in the shim 704 so as to be spaced apart about a circumference of the shim 704. In one example, the shim 704 includes about 12 of the slits 718 and about 12 of the bores 720, however, the shim 704 may include about 4 to about 36 of the slits 718 and about 4 to about 36 of the bores 720. In this example, each slit 718 has a first end 732 defined from the outer periphery 712 to extend radially inward toward the inner periphery 710. Each slit 718 terminates at a second end 734. Each slit 718 has a width W7 of about 0.1 mm to about 1.0 mm, and in one example, is about 0.2 mm to about 0.5 mm. The second end 734 of each slit 718 is in communication with a respective one of the bores 720. Each bore 720 has a center point CP7. Each bore 720 generally has a radius RB3 from the center point CP7, which is less than the radius R1, and in one example, is about 0.5 millimeters (mm) to about 1.5 millimeters (mm), and in this example is about 1.0 millimeters (mm). Generally, the radius RB3 is equal to or larger than the width W7 of the slit 718 to reduce the stress concentration. The slits 718 and the bores 720 increase a flexibility of the shim 704 as compared to the shim 404 and the shim 504.

As the assembly of the shim 704 to the backing layer 200 about the hub 122 and the coupling of the infusion unit 700 to the user is substantially the same as that discussed with regard to the shim 704 of FIGS. 1-4, the assembly of the shim 704 and the coupling of the infusion unit 700 to the user will not be discussed in detail herein. Briefly, the shim 704 is coupled to the backing layer 200 so as to be directly adjacent to the hub 122. With the infusion unit 700 fluidly coupled to the fluid infusion device 102 (FIG. 1), the liner 204 is removed and the infusion unit 700 is coupled to the body of the user so that at least a portion of the fluid outlet 128 extends into the body B of the user and the adhesive patch 208 is coupled to the body B of the user. With the infusion unit 700 coupled to the user, fluid from the fluid reservoir of the fluid infusion device 102 flows through the infusion unit 700 into the body B of the user and the shim 704 resists peeling of the adhesive layer 202 off the body B of the user. The shim 704 is flexible overall, but is locally stiff or rigid between the inner periphery 710 and the outer periphery 712, which improves longevity of the adhesive patch 208 without reducing user comfort. Thus, the shim 704 is also anisotropic, with increased flexibility along a longitudinal axis of the shim 704, and is rigid locally between the inner periphery 710 and the outer periphery 712 (along the second distance 724).

Figure 13:
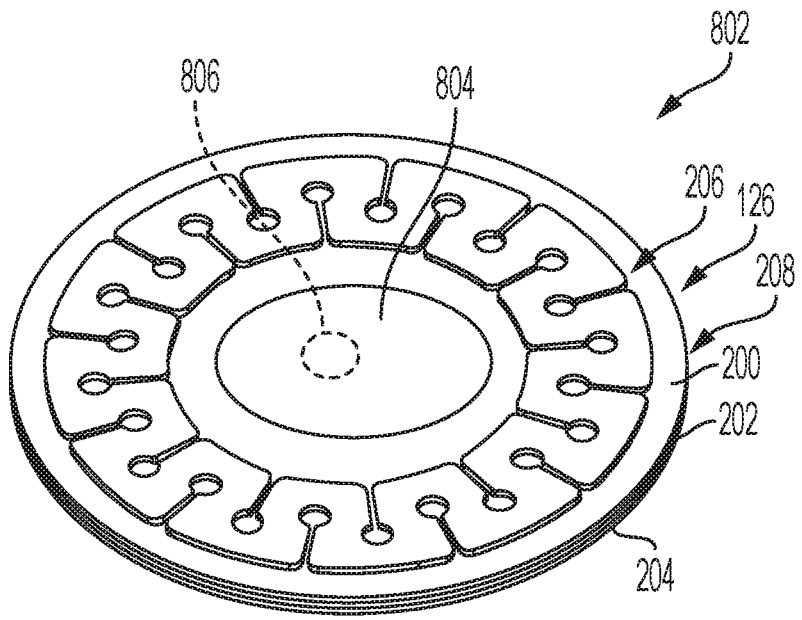
FIG. 13 is a perspective schematic view of a medical device, such as a physiological characteristic sensor, with the shim of FIG. 1 for adhesive patch longevity in accordance with various embodiments.

It should be noted that in still other embodiments, the shim 206 may be configured to extend longevity of an adhesive patch associated with a medical device, such as a physiological characteristic sensor. For example, with reference to FIG. 13, a physiological characteristic sensor 802 is shown. In one example, the physiological characteristic sensor 802 is a glucose sensor, such as a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein). In this example, the physiological characteristic sensor 802 includes a hub or sensor base 804 and a glucose sensor 806 that is coupled to the sensor base 804. The sensor base 804 gives structural support to the glucose sensor 806, and facilitates entry of the glucose sensor 140 into the body of the user. The sensor base 804 may also feature electrical and physical interfaces and elements that accommodate the sensor electronics module (not shown), such as the wireless transmitter that communicates with the infusion pump, the monitor device, or the like. In certain embodiments, the physiological characteristic sensor 802 may include the monitor device coupled to the sensor base 804 such that the physiological characteristic sensor 802 is a continuous glucose monitor. The glucose sensor 806 is an electrochemical sensor that includes the glucose oxidase enzyme, as is well understood by those familiar with glucose sensor technology. The glucose oxidase enzyme enables the glucose sensor 806 to monitor blood glucose levels in a diabetic patient or user by effecting a reaction of glucose and oxygen.

The physiological characteristic sensor 802 also includes the coupling device 126, which in this example, includes the backing layer 200, the adhesive layer 202, the liner 204 and the shim 206. The backing layer 200, the adhesive layer 202 and the liner 204 cooperate to define the adhesive patch 208 for the physiological characteristic sensor 802, and the shim 206 provides longevity to the adhesive patch 208 by resisting a peeling of the adhesive layer 202 off the body of the user. It should be noted that while the physiological characteristic sensor 802 is shown herein as including the shim 206, the physiological characteristic sensor 802 may include any one of the shim 206', 206", 404, 504, 604, 704. Further, the physiological characteristic sensor 802 may comprise the shim 206''' and the adhesive patch 208''', which are each non-circular or trilobular, if desired.

Figure 14:
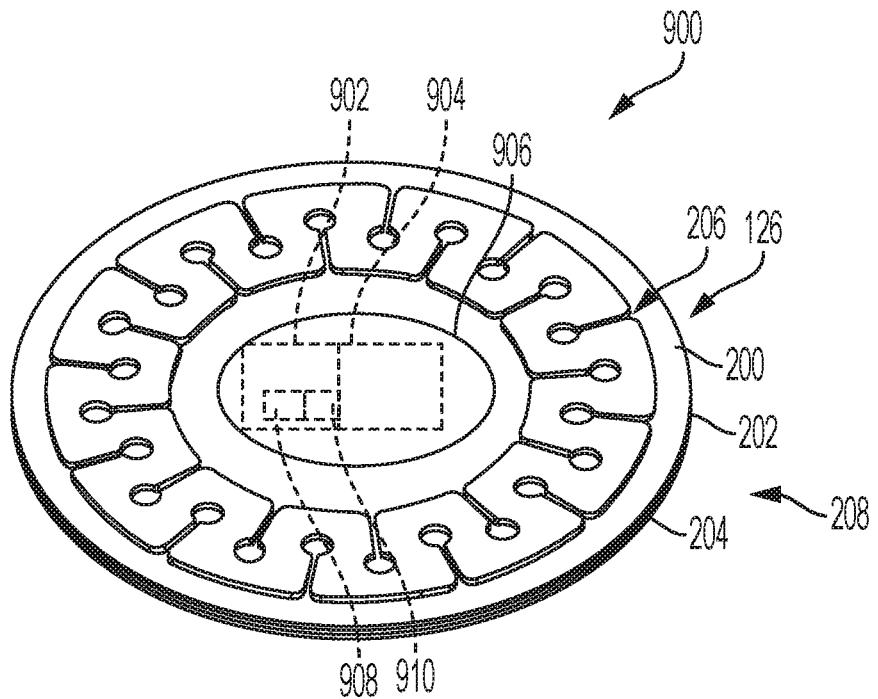
FIG. 14 is a perspective schematic view of a medical device, such as a fluid infusion system, with the shim of FIG. 1 for adhesive patch longevity in accordance with various embodiments.

It should be noted that in still other embodiments, the shim 206 may be configured to extend longevity of an adhesive patch associated with a medical device, such as an infusion unit. For example, with reference to FIG. 14, a medical device, such as a fluid infusion system 900 is shown. In one example, the fluid infusion system 900 includes a fluid infusion device 902 (e.g., an insulin patch pump) and an infusion unit 904, which is disposed within and fluidly coupled to the fluid infusion device 902. The fluid infusion device 902 and the infusion unit 904 are each coupled to a hub 906, and the hub 906 is coupled to the body of the user via the coupling device 126. In this example, the fluid infusion device 902 accommodates an internal fluid reservoir 908 for the fluid to be delivered to the user. A tube 910 represents the fluid flow path that couples the fluid reservoir 908 to the infusion unit 904. When installed as depicted in FIG. 14, the tube 910 extends internally from the fluid reservoir 908 to the internal infusion unit 904, which in turn provides a fluid pathway to the body of the user through a cannula.

The fluid infusion system 900 includes the coupling device 126, which in this example, includes the backing layer 200, the adhesive layer 202, the liner 204 and the shim 206. The backing layer 200, the adhesive layer 202 and the liner 204 cooperate to define the adhesive patch 208 for the fluid infusion system 900, and the shim 206 provides longevity to the adhesive patch 208 by resisting a peeling of the adhesive layer 202 off the body of the user. It should be noted that while the fluid infusion system 900 is shown herein as including the shim 206, the fluid infusion system 900 may include any one of the shim 206', 206", 404, 504, 604, 704. Further, the fluid infusion system 900 may comprise the shim 206''' and the adhesive patch 208''', which are each non-circular or trilobular, if desired. Thus, the shim 206, 206', 206", 404, 504, 604, 704 and the shim 206''' may be employed to provide longevity to an adhesive patch associated with a medical device, including, but not limited to an infusion set, a physiological characteristic sensor, a physiological characteristic sensor monitor and a fluid infusion system.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A medical device, comprising:
a hub;
an adhesive patch coupled to the hub, the adhesive patch to couple the hub to an anatomy, the adhesive patch defining an edge that extends along a perimeter of the adhesive patch; and
an anisotropic shim coupled to the adhesive patch along the perimeter of the adhesive patch proximate the edge to resist an uncoupling of the adhesive patch from the anatomy, the anisotropic shim having an inner periphery spaced apart from an outer periphery, the anisotropic shim is locally rigid between the inner periphery and the outer periphery, the anisotropic shim includes a first slit defined at the outer periphery, the first slit extends radially inward toward the inner periphery and terminates at a first bore defined through the anisotropic shim, a second slit defined at the inner periphery, the second slit extends radially outward toward the outer periphery and terminates at a second bore defined through the anisotropic shim, and the first bore has a first radial distance defined between the first bore and the inner periphery that is different than a second radial distance defined between the second bore and the inner periphery.

2. The medical device of claim 1, wherein the anisotropic shim extends along a longitudinal axis and the anisotropic shim is flexible along the longitudinal axis.

3. The medical device of claim 1, wherein the anisotropic shim has a first side opposite a second side, a thickness defined between the first side and the second side, and the thickness is uniform between the inner periphery and the outer periphery.

4. The medical device of claim 3, wherein the first slit, the first bore, the second slit and the second bore are each defined through the anisotropic shim from the first side to the second side.

5. The medical device of claim 1, wherein the anisotropic shim has a first side opposite a second side, a thickness defined between the first side and the second side, and the thickness varies between the inner periphery and the outer periphery.

6. The medical device of claim 5, wherein the thickness decreases monotonically between the inner periphery and the outer periphery.

7. The medical device of claim 1, wherein the anisotropic shim further comprises a pattern including the first slit, the first bore, the second slit and the second bore that is repeated about a perimeter of the anisotropic shim.

8. The medical device of claim 1, wherein the medical device is an infusion unit, the hub defines a fluid flow path to receive a fluid the infusion unit is fluidly coupled to a fluid infusion device to receive the fluid, the anisotropic shim defines a central bore and the anisotropic shim is coupled to the adhesive patch such that the central bore is positioned about the hub.

9. The medical device of claim 1, wherein the medical device is a physiological characteristic sensor to be coupled to the anatomy to observe a physiological characteristic.

10. The medical device of claim 1, wherein the medical device is a fluid infusion system to be coupled to the anatomy to define a fluid flow path into the anatomy.

11. The medical device of claim 1, wherein the first bore and the second bore are defined through the anisotropic shim between the inner periphery and the outer periphery.

12. The medical device of claim 1, wherein the anisotropic shim is spaced a distance apart from the edge of the adhesive patch.

13. An infusion unit, comprising:
a hub to define a fluid flow path to receive a fluid;
an adhesive patch coupled to the hub, the adhesive patch to couple the hub to an anatomy, the adhesive patch defining an edge that extends along a perimeter of the adhesive patch; and
an anisotropic shim coupled to the adhesive patch along the perimeter of the adhesive patch proximate the edge to resist an uncoupling of the adhesive patch from the anatomy, the anisotropic shim defining a central bore and coupled to the adhesive patch such that the central bore is positioned about the hub, the anisotropic shim extends along a longitudinal axis and has an inner periphery spaced apart from an outer periphery, the anisotropic shim is locally rigid between the inner periphery and the outer periphery and flexible along the longitudinal axis, the anisotropic shim includes at least one first slit defined at the outer periphery, the at least one first slit extends radially inward toward the inner periphery and terminates at a first bore defined through the anisotropic shim, at least one second slit defined at the inner periphery, the at least one second slit extends radially outward toward the outer periphery and terminates at a second bore defined through the anisotropic shim, and the first bore has a first radial distance defined between the first bore and the inner periphery that is different than a second radial distance defined between the second bore and the inner periphery.

14. The infusion unit of claim 13, wherein the hub defines a central axis, the anisotropic shim has a center point defined on the central axis, and the first bore and the second bore are radially offset relative to the center point.

15. An infusion unit, comprising:
a hub to define a fluid flow path to receive a fluid;
an adhesive patch coupled to the hub, the adhesive patch to couple the hub to an anatomy, the adhesive patch defining an edge that extends along a perimeter of the adhesive patch; and
an anisotropic shim coupled to the adhesive patch along the perimeter of the adhesive patch proximate the edge to resist an uncoupling of the adhesive patch from the anatomy, the anisotropic shim spaced a distance apart from the edge of the adhesive patch, the anisotropic shim defining a central bore and coupled to the adhesive patch such that the central bore is positioned about the hub, the anisotropic shim extends along a longitudinal axis and has an inner periphery spaced apart from an outer periphery, the inner periphery spaced apart from the hub by a distance, the anisotropic shim is locally rigid between the inner periphery and the outer periphery and flexible along the longitudinal axis, the anisotropic shim includes at least one first slit defined at the outer periphery, the at least one first slit extends radially inward toward the inner periphery and terminates at a first bore defined through the anisotropic shim, at least one second slit defined at the inner periphery, the at least one second slit extends radially outward toward the outer periphery and terminates at a second bore defined through the anisotropic shim, the first bore has a first radial distance defined between the first bore and the inner periphery that is different than a second radial distance defined between the second bore and the inner periphery, and the first bore and the second bore are defined through the anisotropic shim between the inner periphery and the outer periphery.

\* \* \* \* \*